United States Patent
Fukushima et al.

(10) Patent No.: US 6,669,651 B1
(45) Date of Patent: Dec. 30, 2003

(54) NON-INVASIVE BRAIN FUNCTION EXAMINATION

(75) Inventors: Shogo Fukushima, Moriguchi (JP); Kenshi Suzuki, Osaka-fu (JP); Shuji Murakami, Takaishi (JP); Ryouji Nakajima, Hirakata (JP); Ichiro Fukumoto, Nagaoka (JP); Hisashi Uchiyama, Nagaoka (JP)

(73) Assignee: Matsushita Electric Works, Ltd., Kadoma (JP)

( * ) Notice: Subject to any disclaimer, the term of this patent is extended or adjusted under 35 U.S.C. 154(b) by 0 days.

(21) Appl. No.: 09/693,898

(22) Filed: Oct. 23, 2000

(30) Foreign Application Priority Data

Feb. 24, 2000 (JP) .................................... 2000-047011
May 15, 2000 (JP) .................................... 2000-142409

(51) Int. Cl.[7] ............................................. A61B 13/00
(52) U.S. Cl. ..................................... 600/558; 351/200
(58) Field of Search ................................ 600/558, 544; 351/200–297

(56) References Cited

U.S. PATENT DOCUMENTS

| | | | |
|---|---|---|---|
| 4,850,691 A | * 7/1989 | Gardner et al. | ............. 351/221 |
| 5,422,690 A | 6/1995 | Rothberg et al. | |
| 5,535,760 A | * 7/1996 | Potter | .......................... 128/898 |
| 5,778,893 A | * 7/1998 | Potter | .......................... 128/898 |
| 5,956,125 A | * 9/1999 | Rosse et al. | ................ 351/221 |
| 6,024,707 A | * 2/2000 | Scinto et al. | ................ 600/558 |

FOREIGN PATENT DOCUMENTS

| | | |
|---|---|---|
| EP | 0 743 041 | 11/1996 |
| JP | 7-163522 | 6/1995 |
| WO | WO 96/03070 | 2/1996 |

OTHER PUBLICATIONS

T. Funatsu, et al., Bulletin of the Faculty of Literature, vol. 14, No. 3, pps. 21–31, "New Electronic Scanning Pupillometer, Model KS–1," 1973.
K. Matsunaga, Psychologia, vol. 16, No. 2, pps. 115–120, "A New Binocular Electronic Scanning Pupillometer," Jun. 1973.
T. W. Anderson, The Statistical Analysis of Time Series, Second Edition, John Wiley and Sons, pps. 1–675 (the whole book), "An Introduction To Multivariate Statistical Analysis," 1984.

(List continued on next page.)

Primary Examiner—Max F. Hindenburg
Assistant Examiner—Pamela L Wingood
(74) Attorney, Agent, or Firm—Oblon, Spivak, McClelland, Maier & Neustadt, P.C.

(57) ABSTRACT

A brain function examining apparatus and others for performing an examination of a brain function by detecting a pupillary size of a subject's pupil are provided. The brain function examining apparatus includes a light source for illuminating the pupil, a pupillary detector for detecting the pupillary size, an index calculator for calculating, based on the pupillary size detected by the pupillary detector, a subject index indicative of a characteristic of the pupil, a database for storing a base index indicative of a characteristic of the pupil that can be used as reference, and an output unit for outputting the subject index, calculated by the index calculator, and the base index stored in the database.

26 Claims, 27 Drawing Sheets

OTHER PUBLICATIONS

Leonard F.M. Scinto, et al., Science, vol. 266, pp. 1051–1054, "A Potential Noninvasive Neurobiological Test for Alzheimer's Disease", Nov. 11, 1994.

Xuemin Shi, et al., Medical Electronics and Bio–Engineering, vol. 36, No. 3, pp. 210–214 "A Study for Objective Measurement of the Senile Dementia by Light–Reflex", 1998 (with partial English translation).

Tetsu Ishikawa, et al., Denshi Dokokei Wahkushoppu (Electronic Pupil–meter Workshop), Neuro–ophthalmol.Jpn., vol. 10, No. 2, pp. 106–110, "Popular Electronic Iris–Meter Iriscoder C–2514", 1993 (with partial English translation).

Kiyoshi Hoshino, Television Society Bulletin, vol. 48, no. 8, pp. 1036–1042, "A Mathematical Model for Pupillary Light Response with Regard to Special Morphology of Pupillary Smooth Muscles", 1994 (with English Abstract).

* cited by examiner

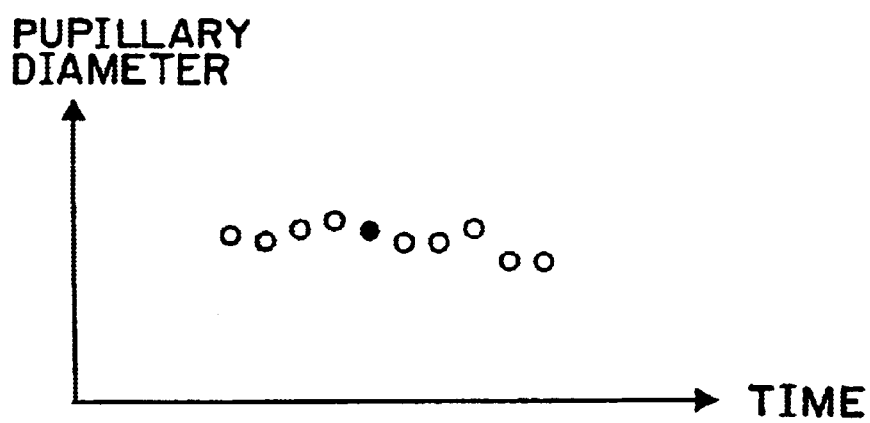

PUPILLARY CHANGE
(SUBJECT XA)

PUPILLARY CHANGE
(SUBJECT XB)

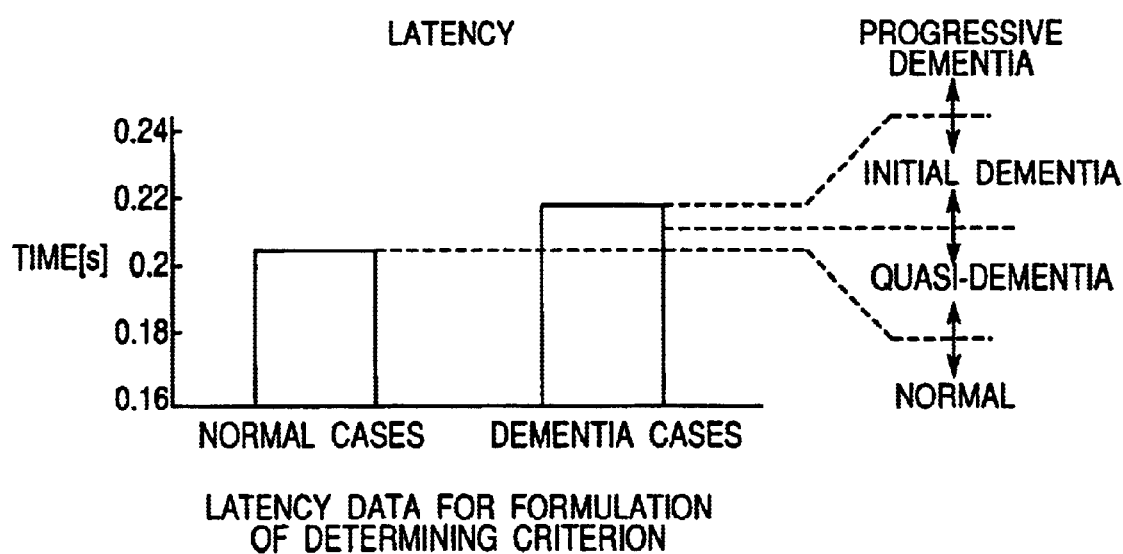

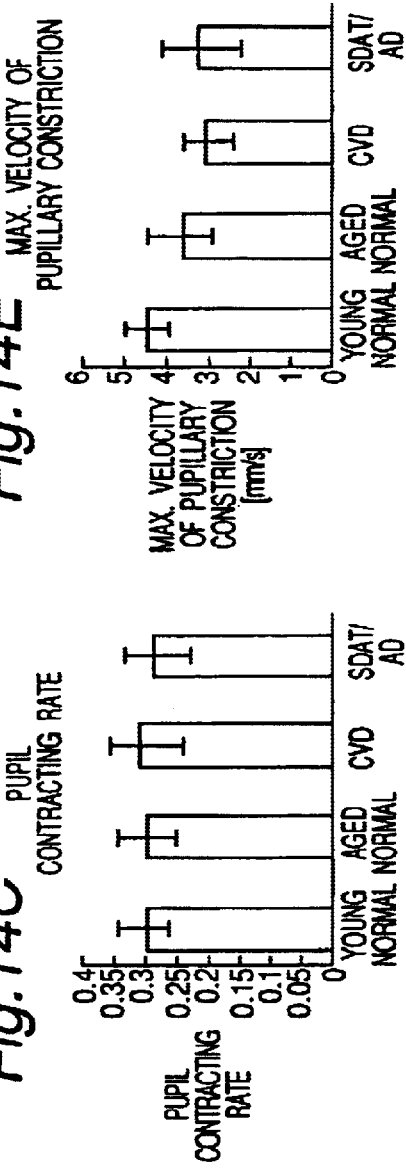
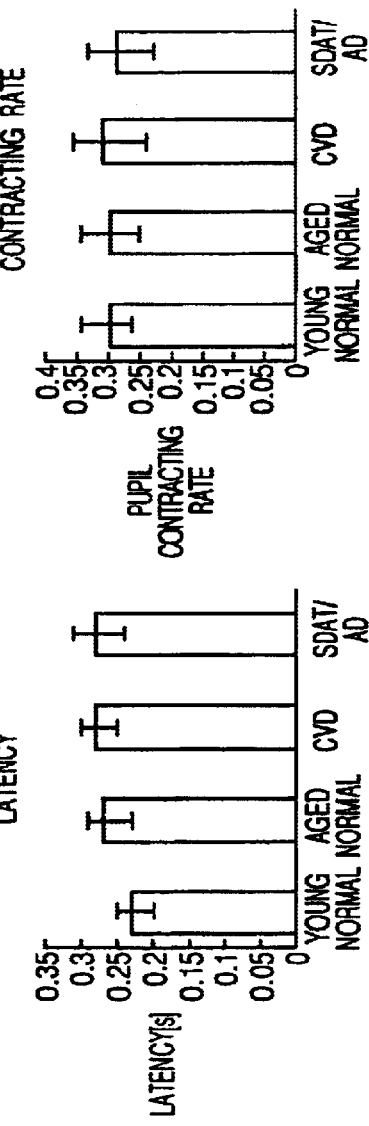
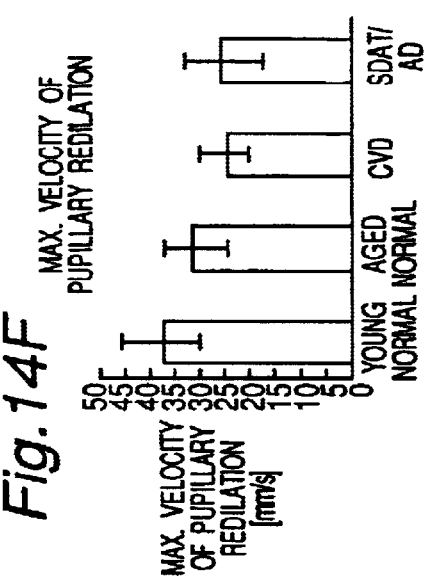
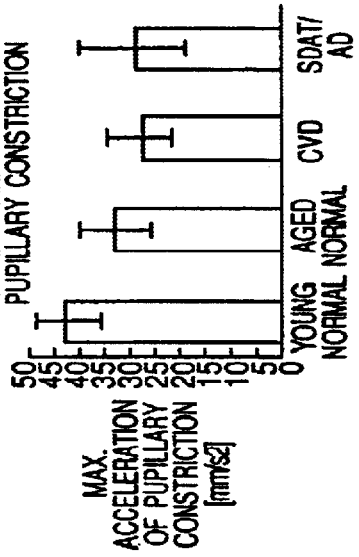
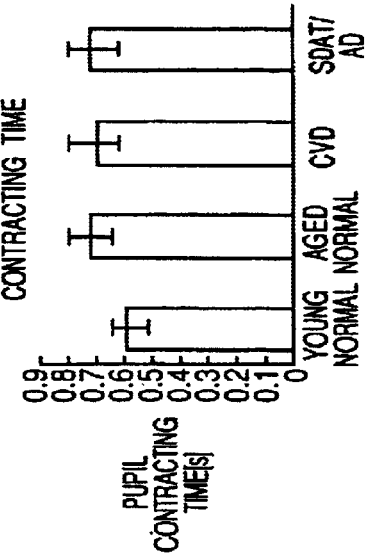

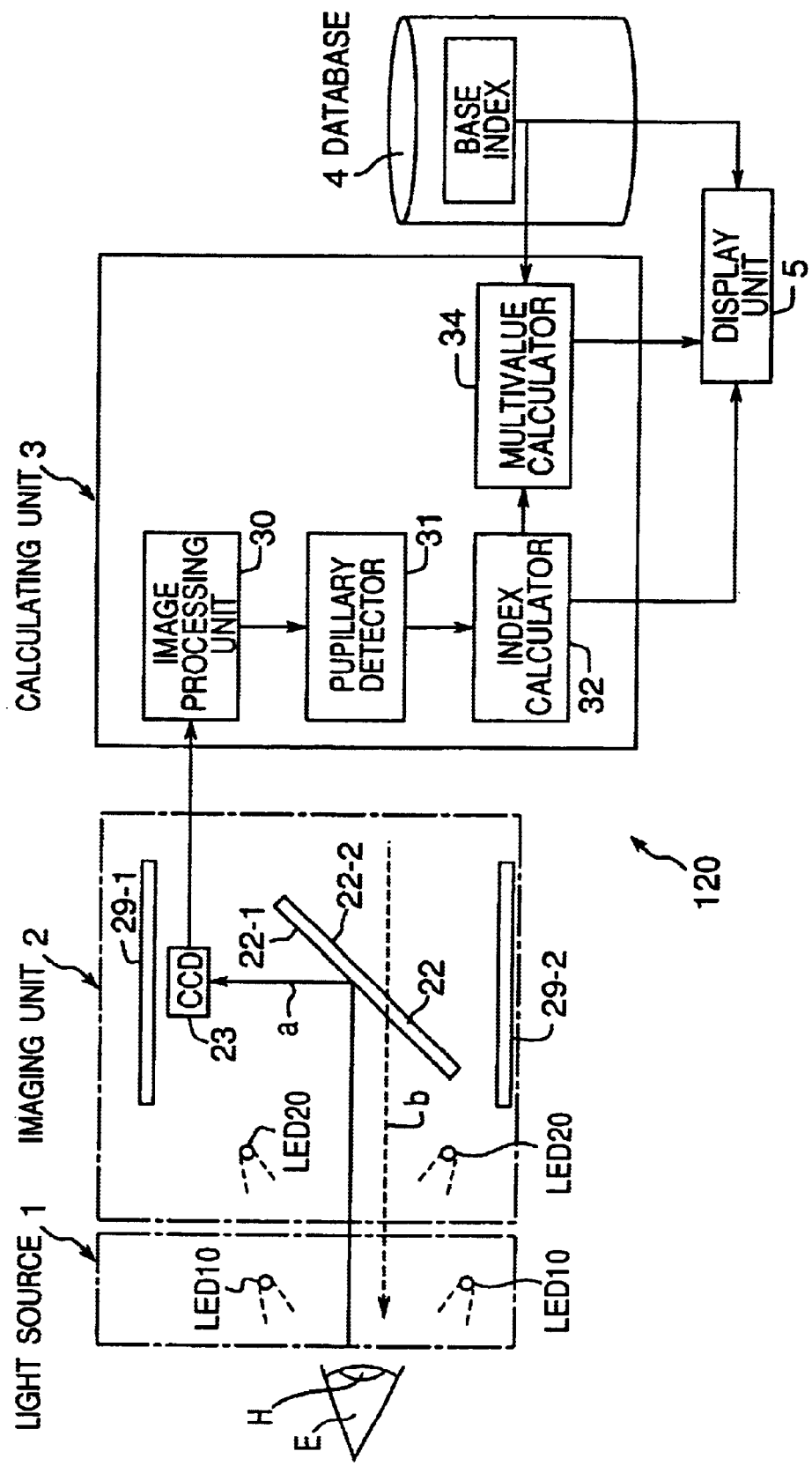

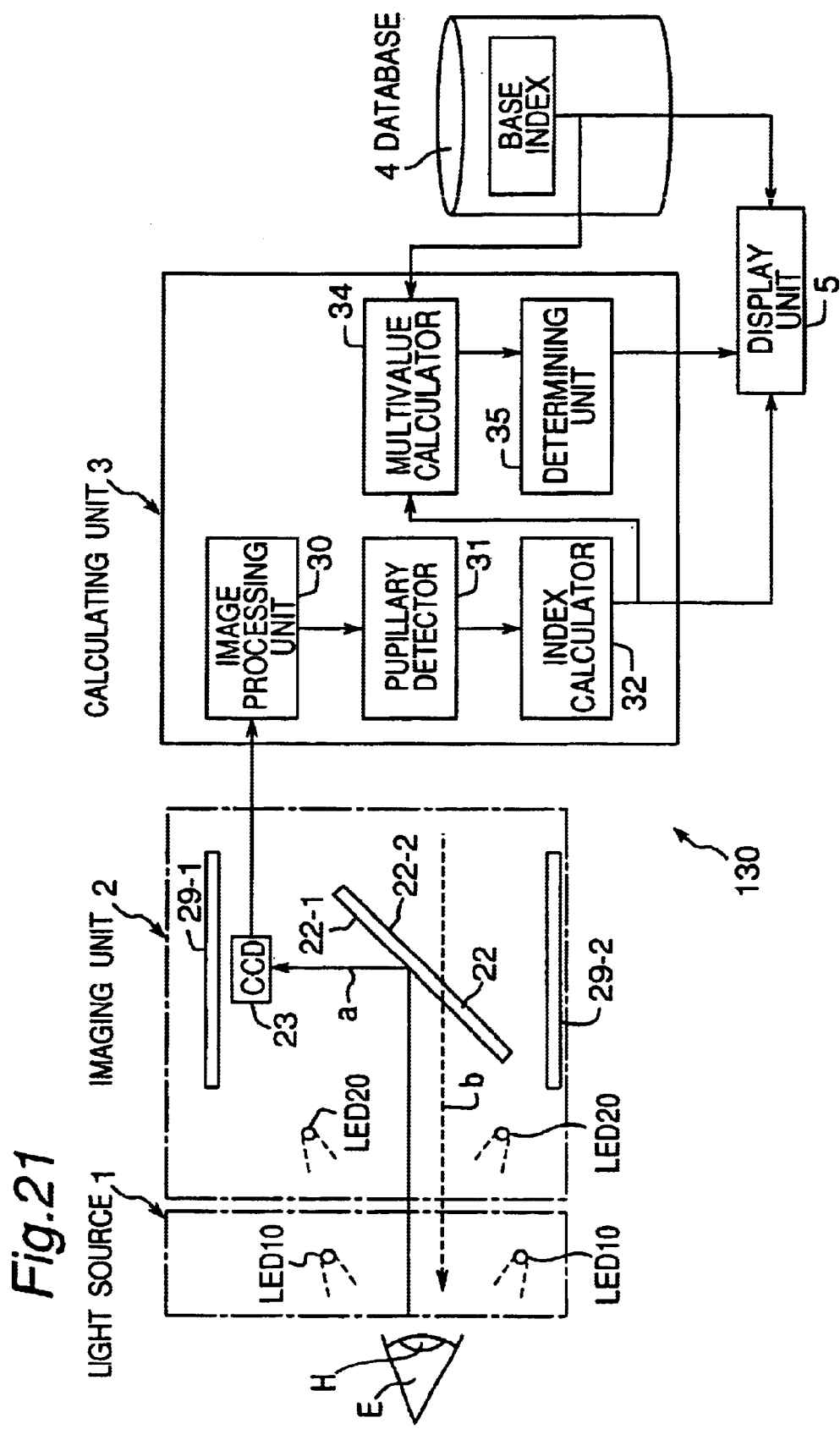

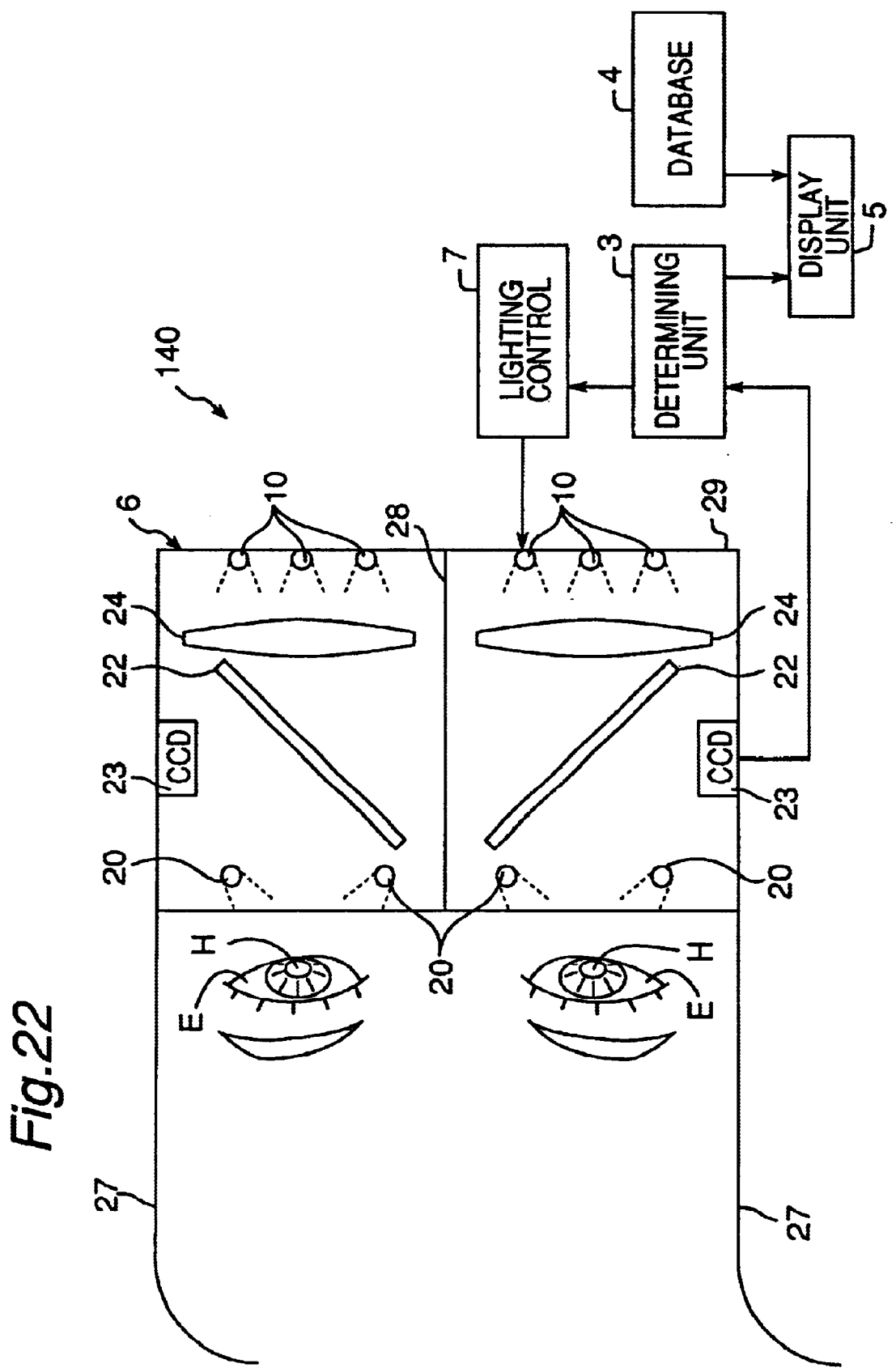

NON-INVASIVE BRAIN FUNCTION EXAMINATION

BACKGROUND OF THE INVENTION

1. Field of the Invention

The present invention relates to a brain function examination by the utilization of a pupillary light reflex. More specifically, the present invention relates to a brain function examining apparatus and a method therefor, wherein the pupillary light reflex exhibited by a subject is detected to determine a cerebral disorder such as, for example, the degree of senescence of the brain, disorder of the autonomic nervous system, the dementia or the like.

2. Description of the Prior Art

It is generally said that the size of a pupil decreases with age (for example, Ishikawa, et al., "Fukyuu-gata Denshi Doukoukei Irisukohda (C-2514) ni Tsuite (On Handy Electronic Pupil Meter Iriscorder (C-2514))", (Shinkei Ganka (Neuro-Ophthalmology), Vol. 10, No. 2, pp. 106–110, 1993). The smooth muscle that adjusts the size of the pupil is governed by the autonomic nervous system and the size of the pupil and/or the pupillary change reflect the degree of activity of the autonomic nervous system.

It is also pointed out that the pupil is associated with the Alzheimer's disease which is generally considered closely associated with the brain function. L. F. M. Scinto, et al. have reported that by measuring the rate of dilation of the pupil before and after a dilating agent is instillated, diagnosis of the Alzheimer's disease which is considered one of dementia is possible ("A Potential Noninvasive Neurobiclogical Test for Alzheimer's Disease", Science, 266, pp. 1051–1054, 1994). According to this method (hereinafter referred to as an instillation method), since diagnosis of the Alzheimer's disease is done in reference to the rate of dilation of the pupil, the result of such diagnosis is subjective. In this respect, it may be said that the instillation method is more excellent than the interview-based medical examination which tends to result in subjective results. Determination based on the interview-based medical examination includes, for example, The Revised version of Hasegawa Dementia Scale (HDSR) which has hitherto been used in diagnosing dementia. By the way, measurement of the pupil based on the installation method requires 30 minutes and cannot be applied to some of subjects suffering from ophthalmic diseases.

To overcome the above discussed inconveniences, a diagnosis technique is available in which the characteristic of the pupil (the pupillary light reflex) is measured to determine if dementia is apparent. This is based on researchers' report that the normal and dementia cases exhibit different pupillary light reflexes (Shi, et al., "A Study for Objective Measurement of the Senile Dementia by Light-Reflex", Iyou Densi to Seitai Kougaku (Medical Electronics and Bioengineering), Vol. 36, No. 3, pp. 210–214, 1998). According to this diagnosing method, unlike the installation method, measurement of the pupillary light reflex completes in a short time and has an advantage that the measurement brings no side-effect.

However, according to the Fumi, et al. report, the normal and dementia cases are merely compared with each other by calculating predetermined indexes (pupillary constricting rate, pupillary constricting time and pupillary redilating rate) indicative of the pupillary light reflex. Accordingly, it is not possible to output (display), for example, a subject index and an average index for the dementia cases and then to utilize a relative relationship displayed in determining if the subject is suffering from dementia or the like. Also, since the pupillary light reflex varies from person to person as is the case with physiological indexes, it cannot be said that with only the three indexes reported by Fumi, et al. the manner of pupillary change is sufficiently grasped. Accordingly, determination of the dementia, the degree of autonomic activity, the degree of senescence of the brain function or the like with the use of such small indexes lacks reliability.

On the other hand, it is not wise to increase the number of the indexes representative of the pupillary light reflex. While increase of the indexes will result in increase of the accuracy of diagnosis, the fact that many indexes must be taken into consideration will make it difficult to achieve a targeted determination. Also, in view of any possible adverse influence strongly brought about by the particular indexes, it may occur that obviously contradictory results of determination will occur. In such case, it may be very difficult to employ which one or ones of results of determination of what index.

SUMMARY OF THE INVENTION

The present invention provides a brain function examining apparatus for performing an examination of a brain function by detection of a pupillary size of a subject, which apparatus comprises: a light source for illuminating a pupil of the subject; a pupillary detector for detecting the pupillary size; an index calculating unit for calculating a subject index indicative of a characteristic of the pupil based on the pupillary size detected by the pupillary detector; a database for storing a base index indicative of a characteristic of a pupil that can be used as a reference; an output unit for outputting the subject index, calculated by the index calculating unit, and the base index stored in the database.

For example, the characteristic of the pupil is a quality associated with variation of the pupillary size and wherein the subject index calculated by the index calculating unit includes at least one of a natural size of the pupil, latency, pupillary redilating time, the amplitude of pupillary constriction, pupil constricting rate, pupil constricting velocity, maximum velocity of pupillary constriction, pupil redilating velocity, maximum velocity of pupillary redilation, pupillary constricting acceleration, maximum acceleration of pupillary constriction, time required to attain the maximum velocity of pupillary constriction, time required to attain the maximum velocity of pupillary redilation, and time required to attain the maximum acceleration of pupillary constriction.

For example, examination of the brain function is that of dementia, and/or examination of the brain function is that of a degree of brain senescence.

Preferably, the brain function examining apparatus further comprises a determining unit for comparing the subject index, calculated by the index calculating unit, with the base index stored in the database to determine a condition of the subject's brain function.

Preferably, the output unit also outputs a result of determination performed by the determining unit.

Preferably, the brain function examining apparatus further comprises a multivalue calculator for calculating discriminant scores based on a plurality of input values, the number of said calculating discriminant scores being smaller than that of the input values; wherein the index calculating unit calculates a plurality of subject indexes and the database stores a plurality of base indexes; and wherein the multivalue calculator calculates subject discriminant scores using the subject indexes, calculated by the index calculating unit, and the base indexes stored in the database, as the input values.

Preferably, the multivalue calculator calculates base discriminant scores using the base indexes as the input values, and further comprising a determining unit for comparing the subject discriminant scores, calculated by the multivalue calculator, and the base discriminant scores to determine a condition of the subject's brain function.

Preferably, the output unit outputs at least one of the subject discriminant scores calculated by the multivalue calculator, the base discriminant scores and a result of determination performed by the determining unit.

Preferably, the database stores as the base index, the index indicative of the characteristic of the pupil of one of a normal case, an autonomic disorder case, a dementia case and an Alzheimer-type dementia case.

Preferably, the determining unit performs determination of one of a degree of senescence, autonomic activity, dementia and Alzheimer's disease of the subject.

For example, the light source emits a step light to the pupil, a flash light to the pupil. Preferably, the light source emits the flash light to the pupil for a duration shorter than a pupillary response latency and/or the light source emits a bundle of light of a size smaller than a minimum possible pupillary size.

Preferably, the pupillary detector detects a time-based change of the pupillary size of the subject and wherein the index calculator is operable to determine a time-based change of an average pupillary size by calculating a mean of a plurality of time-based changes of the pupillary size detected by the pupillary detector and to calculate the subject index based on the average pupillary size.

Preferably, the pupillary detector detects a time-based change of the pupillary size and wherein the index calculator is operable to determine a time-based change of an average pupillary size by moving-averaging a plurality of time-based changes of the pupillary size detected by the pupillary detector and to calculate the subject index based on the average pupillary size.

Preferably, the determining unit is operable to compare some of the subject indexes with some of the base indexes corresponding thereto and to determine, based on a result of comparison, one of progressive senescence of the subject's brain function and probability of the subject suffering from brain disorder.

Preferably, such some of the subject indexes and such some of the base indexes includes at least two of a natural size of the pupil, latency, pupillary redilating rate, pupil constricting velocity, maximum velocity of pupillary constriction, pupil redilating velocity, maximum velocity of pupillary redilation, pupillary constricting acceleration, and maximum acceleration of pupillary constriction.

Preferably, the determining unit determines one of progressive senescence of the subject's brain function and probability of the subject suffering from brain disorder in the event that at least one of situations in which the natural pupil size of the subject is small, in which the latency is large, in which the pupil constricting velocity is low, in which the maximum velocity of pupillary constriction is low, in which the pupil redilating velocity is low and in which the maximum velocity of pupillary redilation is low establishes.

The present invention provides a method of examining a brain function of a subject by detecting a pupillary size of a pupil of the subject, which method comprises the steps of: illuminating the pupil with light; detecting the pupillary size; calculating a subject index indicative of a characteristic of the pupil based on the pupillary size; storing a base index indicative of a characteristic of a pupil that can be used as a reference; and outputting the subject index calculated and the base index stored.

For example, the characteristic of the pupil is a quality associated with variation of the pupillary size and wherein the subject index calculated by the index calculating unit includes at least one of a natural size of the pupil, latency, pupillary redilating time, the amplitude of pupillary constriction, pupil constricting velocity, pupil constricting rate, maximum velocity of pupillary constriction, pupil redilating velocity, maximum velocity of pupillary redilation, pupillary constricting acceleration, maximum acceleration of pupillary constriction, time required to attain the maximum velocity of pupillary constriction, time required to attain the maximum velocity of pupillary redilation, and time required to attain the maximum acceleration of pupillary constriction.

Preferably, the method of examining the brain function as claimed in claim 21, further comprising a step of performing a multivalue calculation based on a plurality of input values, the number of said calculating discriminant scores being smaller than that of the input values; wherein the calculating step is a step of calculating a plurality of subject indexes, the storing step is a step of storing a plurality of base indexes, and the calculating step is a step of calculating subject discriminant scores using the subject indexes, calculated by the index calculating unit, and the base indexes stored in the database, as the input values.

Preferably, the calculating step is a step of calculating base discriminant scores using the base indexes as the input values, and further comprising a step of comparing the subject discriminant scores calculated and the base discriminant scores to determine a condition of the subject's brain function.

Preferably, the storing step is a step of storing as the base index, the index indicative of the characteristic of the pupil of one of a normal case, an autonomic disorder case, a dementia case and an Alzheimer-type dementia case.

Preferably, the determining step is a step of determining one of a degree of senescence, autonomic activity, dementia and Alzheimer's disease of the subject.

BRIEF DESCRIPTION OF THE DRAWINGS

The present invention will become readily understood from the following description of preferred embodiments thereof made with reference to the accompanying drawings, in which like parts are designated by like reference numeral and in which:

FIGS. 6A and 6B illustrate respective examples of a moving-averaging process;

FIG. 13 illustrates an example of the determining criterion formulated;

FIGS. 14A to 14F illustrate different results of measurement conducted for formulation of the determining criterions associated with predetermined indexes;

FIG. 17 is a diagram showing the brain function examining apparatus according to a third preferred embodiment of the present invention;

FIG. 21 is a diagram showing the brain function examining apparatus according to a fourth preferred embodiment of the present invention;

FIG. 22 is a diagram showing the brain function examining apparatus including a pupillary measuring device according to this embodiment;

DESCRIPTION OF THE EMBODIMENTS

First Embodiment

Figure 1:
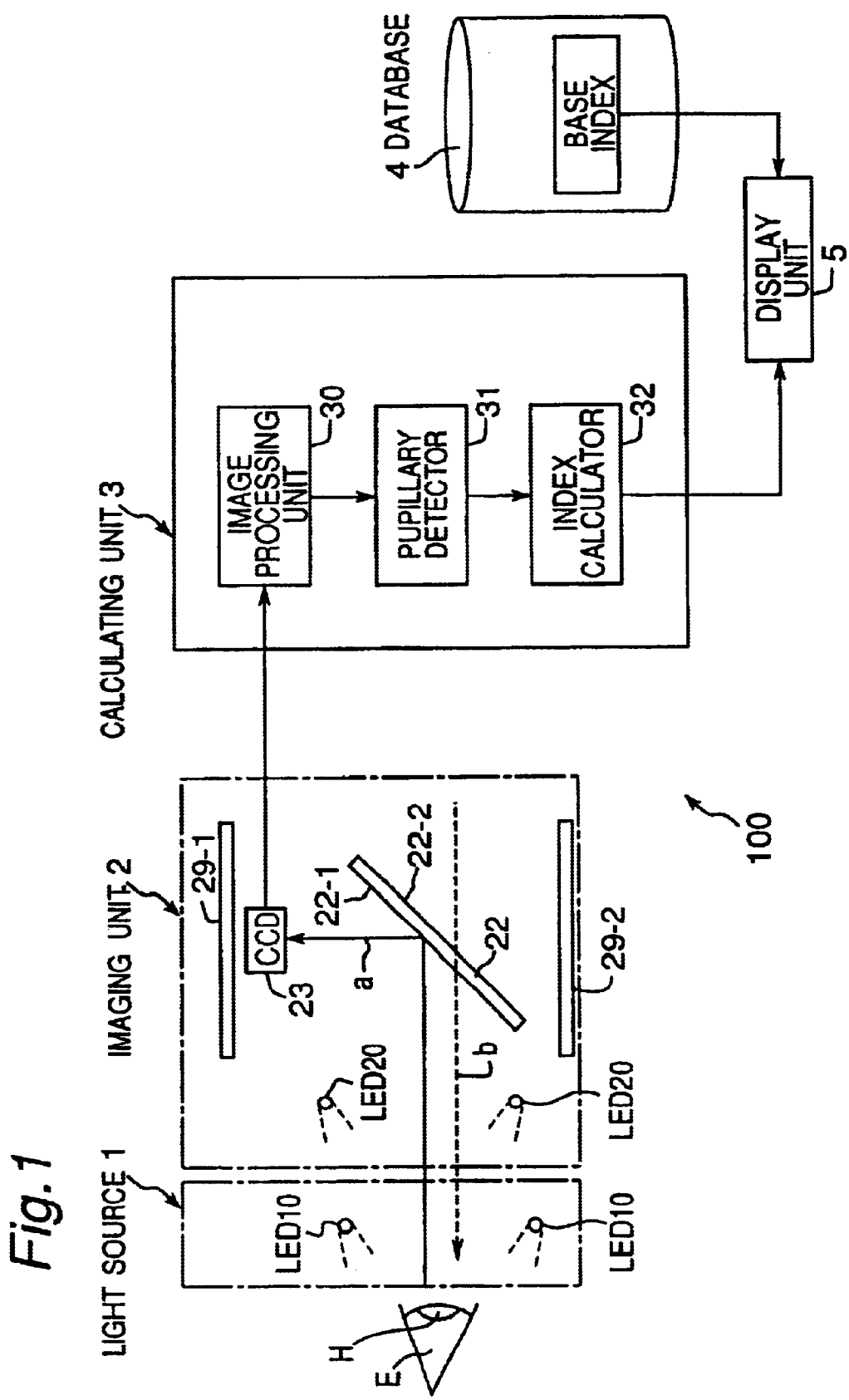
FIG. 1 illustrates the structure of a brain function examining apparatus according to a first preferred embodiment of the present invention.

Referring now to FIG. 1, there is shown an non-invasive brain function examining apparatus 100. This examining apparatus 100 includes a light source 1 for applying a light stimulus to an eye E of a patient to be examined, an imaging unit 2, an arithmetic unit 3, a database 4 and a display unit 5. This examining apparatus 100 is operable to collect data from a pupil H of the patient's eye E data necessary to examine the brain function. Specifically, the examining apparatus 100 is operable to emit light to the patient's eye E to cause the pupil H to vary in size in response to the light so that the variation can be detected for calculating indexes descriptive of the characteristic of the patient's pupil H. The examining apparatus 10 is also operable to display not only the calculated indexes, but also respective indexes associated with normal and dementia cases that are stored in the examining apparatus 100. With the examining apparatus 100, diagnosis can be made to determine if the patient having been examined is a normal person or a suspected dementia case and, also, the degree of progress of dementia in the event that the patient is deemed suffering from dementia.

The various component parts of the examining apparatus 100 will now be described. The light source 1 includes a plurality of light emitting diodes (hereinafter referred to as visible LEDs) 10 for emitting white light of a visible wavelength region towards the patient's eye. E. The visible LEDs 10 when turned on or turned off in response to a control signal fed from a lighting control (not shown) are utilized to induce the pupillary light reflex from the pupil H.

Figure 2A:
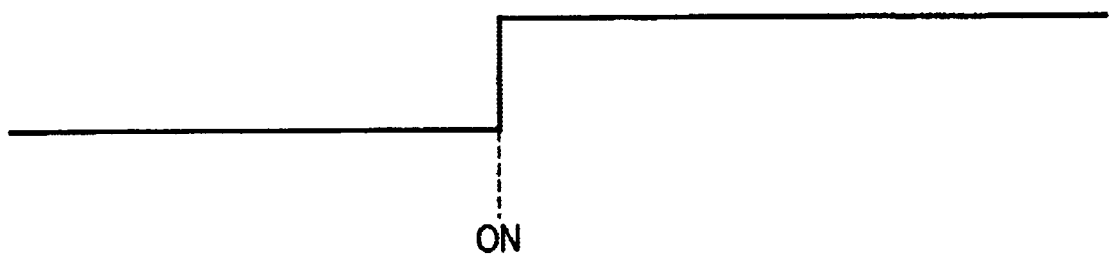
FIG. 2A is a timing chart showing a control signal for emitting a step light.

The light stimulus necessary to induce the pupillary light reflex may be either a step light or a flash light. FIG. 2A illustrates a timing chart of the control signal necessary to emit the step light. The step light referred to herein is of a nature effective to cause the pupil H in a non-stimulated state, with no light stimulus applied, to initiate the pupillary change in response to the light stimulus until the pupil H attains a steady state in which the pupillary change no longer progress and to sustain the pupil H in the steady state during a testing period. It is to be noted that the step light is to be understood as including light of a nature effective to cause the pupil H in a stimulated state, with a certain intensity of light stimulus applied, to initiate the pupillary change in response to a reduced or increased intensity of light stimulus until the pupil H attains a steady state in which the pupillary change no longer progress and to sustain the pupil H in the steady state during a testing period. The visible LEDs 10 shown in FIG. 1 are turned on in response to a set-up of the control signal as shown in FIG. 2A.

Figure 2B:
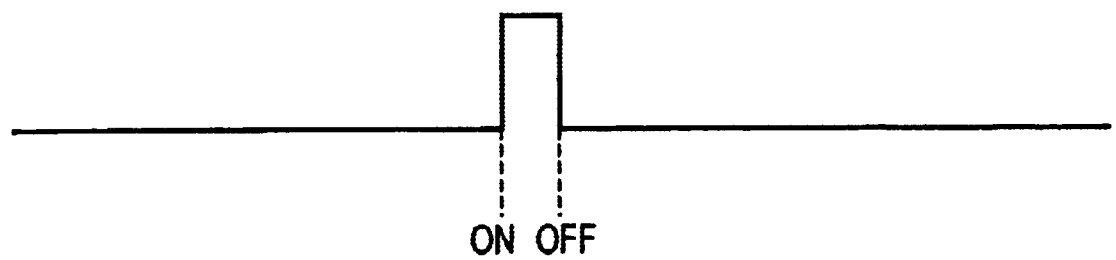
FIG. 2B is a timing chart showing a control signal for emitting a flash light.

FIG. 2B illustrates a timing chart of the control signal necessary to emit the flash light. The flash light referred to herein is of a nature that is turned on, while the pupil H is in the non-stimulated state, for a short period and is immediately turned off. The visible LEDs 10 shown in FIG. 1 are turned on and off in response to the set-up and set-down of the control signal, respectively, as shown in FIG. 2B. As is the case with the step light, the flash light is to be understood including light effective to provide the light stimulus of an intensity increasing or decreasing only for a short period while the pupil H is in the stimulated state, but the flash light can effectively utilized to provide the light stimulus while the pupil H is in the non-stimulated state. This is because it has been empirically ascertained that application of the light stimulus while the pupil H is in the non-stimulated state is effective to enable the pupillary change to be observed clearly.

With the step light shown in FIG. 2A, control of the light stimulus can easily be accomplished since the light stimulus presented at a certain timing may be retained in a state as presented, and can be attained when a person may turn on an ignition switch. In contrast thereto, with the flash light shown in FIG. 2B, it is necessary to strictly control the turn-on duration of the light stimulus. This is necessitated particularly where the same light stimulating condition has to be presented to a number of subjects. As discussed hereinbefore, lighting and extinction can be controlled by the lighting control (not shown). It is, however, to be noted that each visible LED 10 shown in FIG. 1 may include any other light emitting element including a colored-light emitting element provided that the pupillary light reflex can be induced.

Referring to FIG. 1, the imaging unit 2 is utilized to monitor the subject's eye E including the pupil H and to output an image date descriptive of the image of the subject's eye E. This imaging unit 2 includes a plurality of infrared emitting diodes (Ir LEDs) 20, a translucent mirror 22, a CCD camera 23, and first and second light shielding plates 29-1 and 29-2. The infrared LEDs 20 are those for emitting infrared rays of light. Imagewise rays of light reflected from the subject's eye E as a result of the eye E having been illuminated by the infrared light travel along an optical path a towards the CCD camera 23 after having been reflected by the translucent mirror 22. The use of the infrared light is for the purpose of restricting to the light stimulus to be applied to the pupil H to the visible light projected by the visible LEDs 10. Since the human retina is insensitive to the infrared light, the infrared light when projected towards the eye E does not induce any pupillary light reflex and, therefore, the subject will not perceive brightness of the infrared light. However, any light emitting elements may be employed provided that the subject's eye E can be imaged without causing the subject to turn his or her attention and without inducing any eye motion.

The translucent mirror 22 is of a kind capable of transmitting a portion of light therethrough and reflecting the remaining portion of light. Thus, the translucent mirror 22 in the illustrated embodiment reflects the imagewise light from the subject's eye E towards the CCD camera 23. The use of the translucent mirror 22 makes it possible for the CCD camera 23 to monitor the subject's eye E while the subject is looking at an outside scene and is, therefore, effective to make the subject feel easy when the subject wears on an measuring instrument including the light source 1 and the imaging unit 2. It is to be noted that an optical path indicated by b in FIG. 1 is a path of travel of external light, carrying an image of the outside scene, towards the subject's eye E. If arrangement is made that an object fixed at the visual range can be viewed through the translucent mirror 22, accomodation factors governing the lens motion within the eyeball which serves a focusing motion can be fixed so that the subject's eye can be measured under severely controlled conditions. In other words, factors resulting in pupillary constriction that is generally referred to as a near reflex that occurs when the eye lens focused on a distant object is adjusted to a near object can advantageously be eliminated. Also, in order for the CCD camera 23 to receive as large an amount of infrared rays of light as possible, the translucent mirror 22 may be of a type having a wavelength selecting capability. With this, the utilization of the infrared light can be maximized. If one (i.e., a surface 22-1) of opposite surfaces 22-1 and 22-2 of the translucent mirror 22, which confronts the subject's eye E and the CCD camera 23, is so surface-treated as to reflect 100% of the incoming infrared light, the entire amount of the incoming infrared light can be advantageously received by the CCD camera 23 with no loss thereof. It is, however, to be noted that the translucent mirror 22 may not be utilized and, in such case, the subject's eye E can be imaged in a dark environment. In the dark environment, nothing falls on the vision and, therefore, there is no stimulus that may induce the lens adjustment.

The CCD camera 23 of the imaging unit 2 monitors the image of the subject's eye E and outputs image data descriptive of the monitored subject's eye E. This CCD camera 23 is of a type sensitive to the infrared light. The use of the CCD camera 23 makes it possible to image the subject's eye E even in the dark environment isolated from the external visible light. Also, in place of the CCD camera 23, any other suitable imaging device such as, for example, CMOS sensor may be employed. Photo-taking may be carried out continuously.

The first light shielding plate 29-1 is so arranged as to shield the CCD camera 23 from the external visible light, to thereby prevent the subject from being conscious of the CCD camera 23. However, if the CCD camera 23 is installed in an environment in which the CCD camera 23 is invisible to the subject, for example, in a dark room, this first light shielding plate 29-1 may be dispensed with. The second light shielding plate 29-2 is used to shield light which would otherwise transmit across the translucent mirror 22 from the surface 22-2 to the surface 22-1, so that no light other than the imagewise light descriptive of the image of the pupil H will fall on the CCD camera 23. It is, however, to be noted that under the environment in which no light other than the imagewise light descriptive of the image of the pupil H will fall on the CCD camera 23, this second light shielding plate 20-2 may not be employed.

Figure 3:
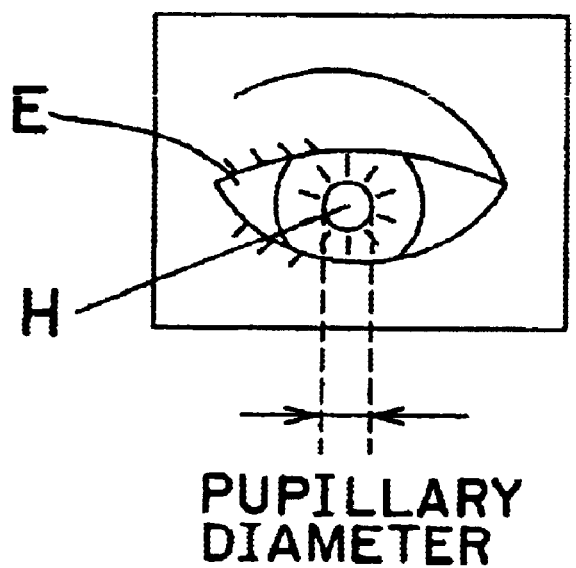
FIG. 3 is a diagram showing a subject's eye E and its pupil H imaged.

With the imaging unit 2 of the structure described above, the subject's eye E can be imaged. As shown in FIG. 3, the subject's eye and pupil so imaged are indicated by E and H, respectively. In FIG. 3, the pupillary diameter is shown as represented by a diameter of the pupil H. If the pupil H is not assumed as having a complete round shape, the pupillary diameter may be represented by either the diameter as measured in a transverse direction or the diameter as measured in a vertical direction of the pupil H.

The calculating unit 3 is operable to calculate indexes indicative of characteristic of the pupil H based on the image data. More specifically, the calculating unit 3 utilizes the image data of the subject's eye E to detect the pupillary diameter. The calculating unit 3 is also operable to perform a predetermined data processing to eliminate measurement noises superimposed on the data detected of the pupillary diameter and to calculate indexes indicative of the pupillary change such as, for example, the velocity of the pupillary constriction, the velocity of the pupillary redilation and so on. It is, however, to be noted that a computer (PC), for example, may be employed for the calculating unit 3 provided that it can perform not only the image processing and the detection of the pupillary diameter from the image data as described above, but also the calculation of the indexes as will be described later.

The calculating unit 3 includes an image processor 30, a pupillary detector 31 and an index calculator 32. The image processor 30 performs both a data processing and a data extraction necessary to permit the pupillary detector 31 to detect the pupillary diameter.

The pupillary detector 31 detects the pupil based on the image data and then determines the size thereof. The pupillary size may be either the diameter if the pupil is of a complete round shape, or the surface area of the pupil. In the description that follows, the term "pupillary diameter" is used as an example of various parameters that define the size of the pupil H.

Various methods have been well known in the art to determine the pupillary diameter from the image data. The most fundamental method is disclosed by K Matsunaga, "Doukou Undouno Shinrigaku (Psychology of Pupillary Motion)", published in 1990 from Nakanishiya Publishing Co., in which a NTSC video signal is utilized to allow an electronic circuit to extract a signal component indicative of an image of the pupil so that the pupillary diameter can be determined. Extraction of the signal component indicative of the pupil image is to extract information associated with the shape of the pupil, for example, information descriptive of the position of an endpoint that defines the pupillary margin. This method is handy and effective to determine the pupillary diameter accurately. The pupillary detector 31 may determine the pupillary diameter at a predetermined timing or may continuously determine the pupillary diameter before, during and after application of the light stimulus. In the latter case, time-dependent change of the pupillary diameter can be obtained.

Figure 4A:
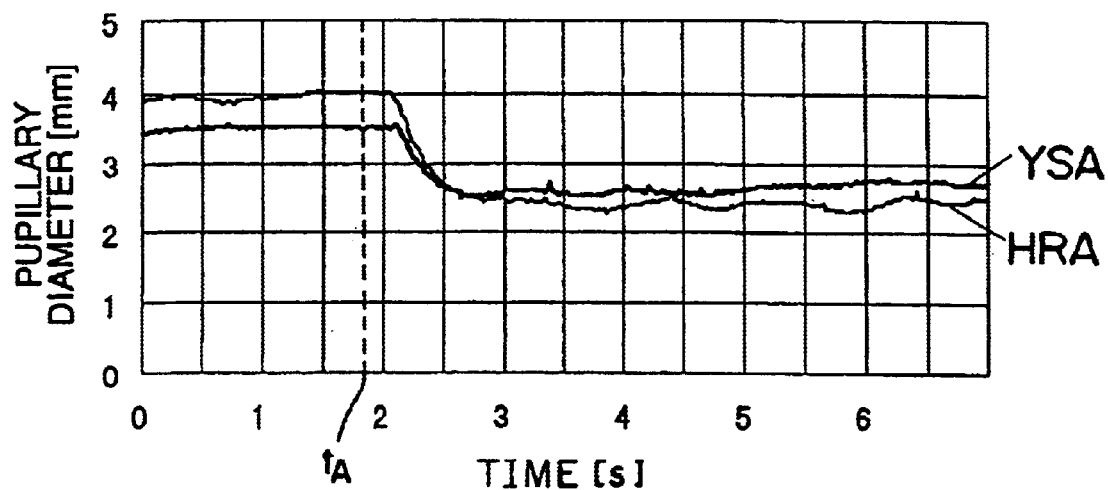
FIG. 4A is a chart showing change of two subjects' pupillary diameters with passage of time when the step light is applied as a light stimulus.
Figure 4B:
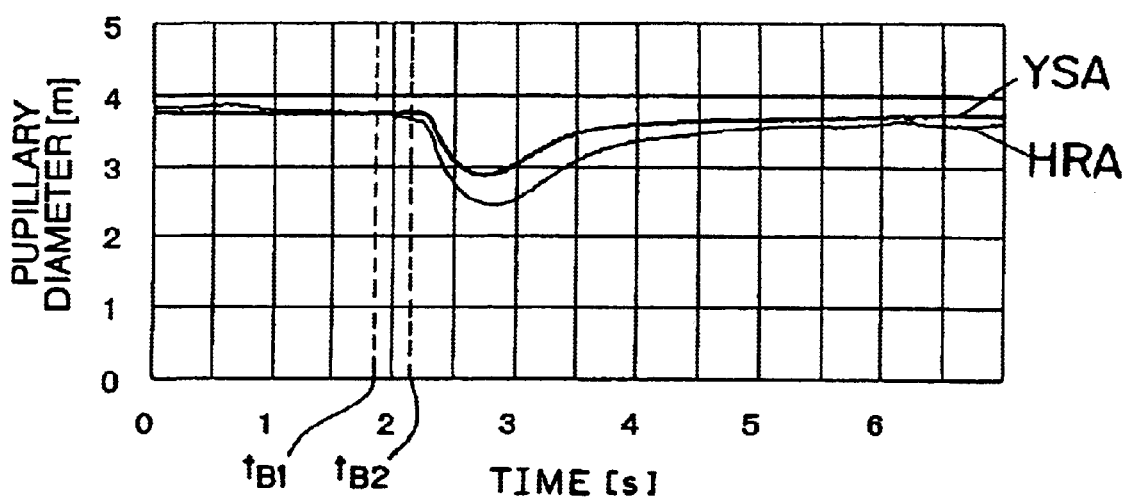
FIG. 4B is a chart showing change of two subjects' pupillary diameters with passage of time when the flash light is applied as a light stimulus.

FIG. 4A illustrates the time-dependent changes of the pupillary diameter exhibited by two subjects HRA and YSA when the light stimulus in the form of the step light as shown in FIG. 2A has been applied. The step light is turned on at a timing T=$t_A$. On the other hand, FIG. 4B illustrates the time-dependent changes of the pupillary diameter exhibited by two subjects HRA and YSA when the light stimulus in the form of the flash light as shown in FIG. 2B has been applied. The flash light is turned on at a timing T=$t_{B1}$ and turned off at a timing T=$t_{B2}$. According to FIGS. 4A and 4B, it is clear that the step light shown in FIG. 2A and the flash light shown in FIG. 2B results in different changes of the pupillary diameter. Specifically, as compared with the graph of FIG. 4A associated with the step light shown in FIG. 2A, the graph of FIG. 4B associated with the flash light shown in FIG. 2B provides a clear point at which the maximum pupillary constriction takes place. While the subject HRA has shown the maximum pupillary constriction occurring at a timing shortly before the time axis 4 [s], the exact point at which the maximum pupillary constriction takes place is not clear. This means that it is difficult to lead out the indexes indicative of the dynamic characteristic of the pupil as will be described later or that an error contained in the indexed will increase. This in turn adversely affects the accuracy with which what disease the subject showing such pupillary change is suffering from is diagnosed.

The difficulty with the step light shown in FIG. 2A in leading out the point of the maximum pupillary constriction depends on the intensity of the light stimulus. In general, the smaller the amount of light of the light stimulus, the clearer the point of the maximum pupillary constriction. Such clearness is not so much as that afforded by the flash light shown in FIG. 2B. With the flash light, except for a short length of time during which the light stimulus is applied, the pupil is in a non-stimulated state and since the factors that induce the pupillary response are found within a very limited time, it may be said that a characteristic of a dynamical pupillary response of a pupillary control mechanism in the brain is observed. In general, the pupillary response requires a time lag (i.e., "latency" as defined later) ranging from about 200 to about 300 msec. subsequent to application of the light stimulus to the pupil. If the flash light of a duration shorter than this time lag or latency, a measurement condition can be set in which the light stimulus no longer exist during the pupillary response taking place. It is to be noted that in the example shown in FIG. 4b, the light stimulus represented by the flash light has a duration of 100 msec., but it may be shorter than 100 msec.

The pupillary detector 31 of the calculating unit 3 shown in FIG. 1 may determine the pupillary diameter by the utilization of either an arithmetic mean or a moving-averaging. Since the measured data on the pupillary diameter which have not processed in any way generally contains measurement noses, it is for the purpose of accurately determining the pupillary diameter. By accurately determining the pupillary diameter, the measurement noises (and influences they may bring about) which would constitute an error factor at the time of leading the indexes indicative of the characteristic of the pupil as will be described later can be minimized. Calculation of the arithmetic mean utilizes the fact that if the measuring noises are assumed to be random noises, they have no correlation with each sample of the measurement data. In contrast thereto, the moving-averaging utilizes the fact that if the measuring noises are assumed to be random noises, they have no correlation with time. Hereinafter, procedures for calculating the pupillary diameter with the use of the arithmetic mean and the moving-averaging will be described.

Figure 5A:
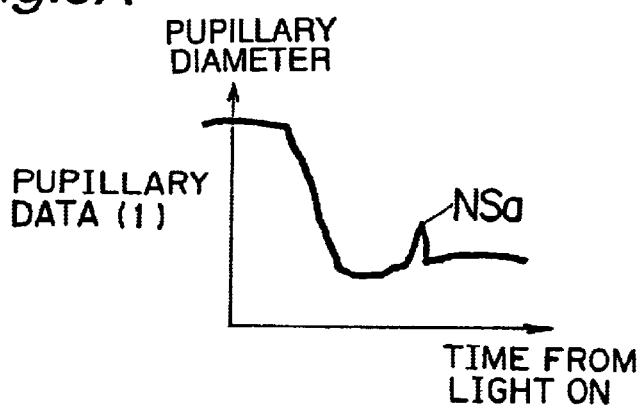
FIGS. 5A to 5C illustrates different data on the pupillary diameter of the same subject under the same measuring condition, respectively.
Figure 5B:
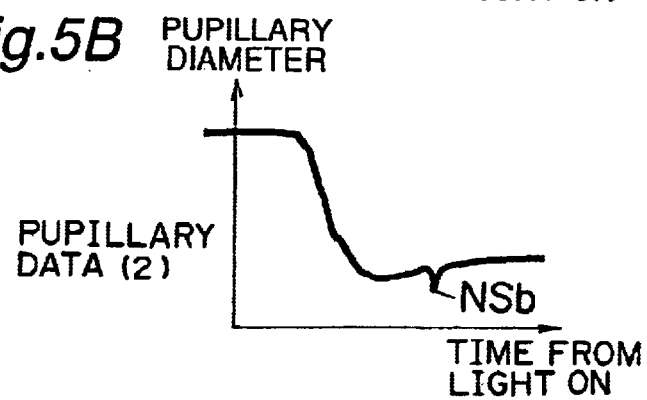
Figure 5C:
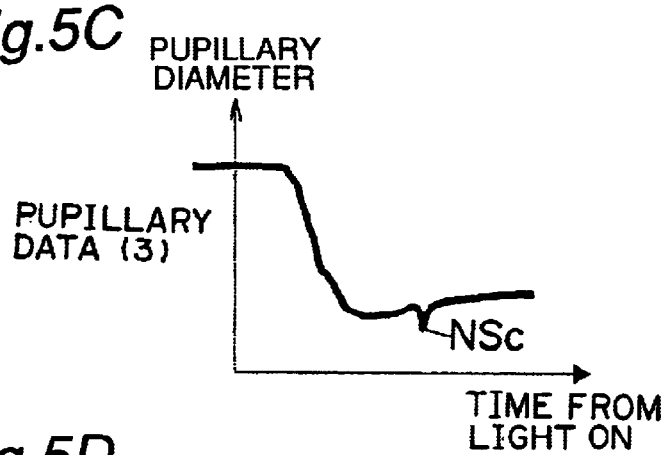

FIGS. 5A to 5D illustrate measured pupillary diameters and the pupillary diameter obtained by calculating the arithmetic mean of the measured pupillary diameters. In order to calculate the arithmetic mean, a plurality of pupillary data (1), (2) and (3) showing respective pupillary changes induced by the same subject and measured under the same testing condition are necessary. Those pupillary data (1), (2) and (3) contain respective noises NSa, NSb and NSc each appearing at the same timing and superimposed on the associated pupillary data. The number of the pupillary data is referred to as order. Thus, the order of the data shown in FIGS. 5A to 5C is three. The noise NSa is a relatively high noise in a positive direction; the noise NSb is a relatively low noise in a negative direction; and the noise NSc is a relatively low noise in the negative direction.

Figure 5D:
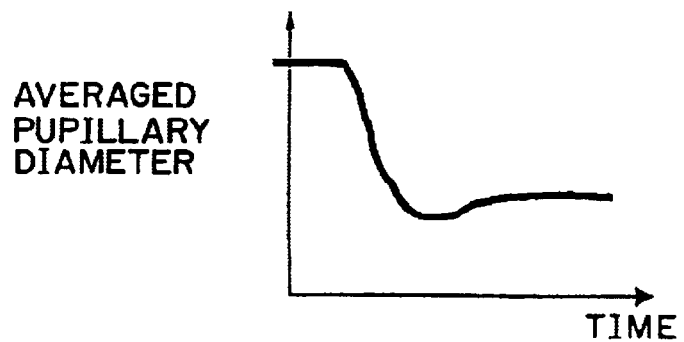
FIG. 5D illustrate data on the pupillary diameter obtained by an averaging process.

Those pupillary data (1) to (3) are summed together with respect to the timing at which application of the light stimulus has started and are then divided by the order three to provide the data on the pupillary diameter that has been averaged as shown in FIG. 5D. FIG. 5D makes it clear that the positive and negative noises have been counterbalanced and, therefore, the data on the pupillary diameter is not so much adversely affected by the noises. Even where the order is different, calculation of the arithmetic mean may be performed in a manner similar to that described above.

FIGS. 6A and 6B illustrate examples of the moving-averaging. The moving-averaging is a process in which the pupillary data at a certain timing in a time series of the pupillary data and the pupillary data before and after such certain timing are added together and are then divided by the number of the pupillary data summed together so that the pupillary data obtained by the division can be used as descriptive of the pupillary diameter at that timing. If using the measured data of the pupillary diameter shown in FIG. 6A, the total five pupillary data including the pupillary data at a certain timing shown by ● and four pupillary data before and after the certain timing are moving-averaged, the pupillary data after the moving-averaging can be obtained. FIG. 6B illustrates the pupillary data obtained by the moving-averaging. The order of the moving-averaging is five. Even where the order is different, the moving-averaging may be performed in a manner similar to that described above.

Other methods of detecting the pupillary diameter includes determination of the pupillary diameter with the use of an image processing software to a digitized image of the pupil. It is, however, to be noted that if the amount of data (resolution) the image processing software can process is lower than the resolution of the CCD camera 23 shown in FIG. 1, no maximized use of the resolution of the CCD camera 23 can be possible. Any method of detecting the pupillary diameter such as, for example, a scleral reflection method, may be employed other than the method utilizing the image data. The scleral reflection method is wherein the size of the pupil is induced based on the amount of infrared light projected onto and then reflected from an eyeball surface. This scleral reflection method is based on the finding that the reflectivity of the pupil with respect to the infrared light differs from that of the iris around the pupil and the sclera.

Figure 7:
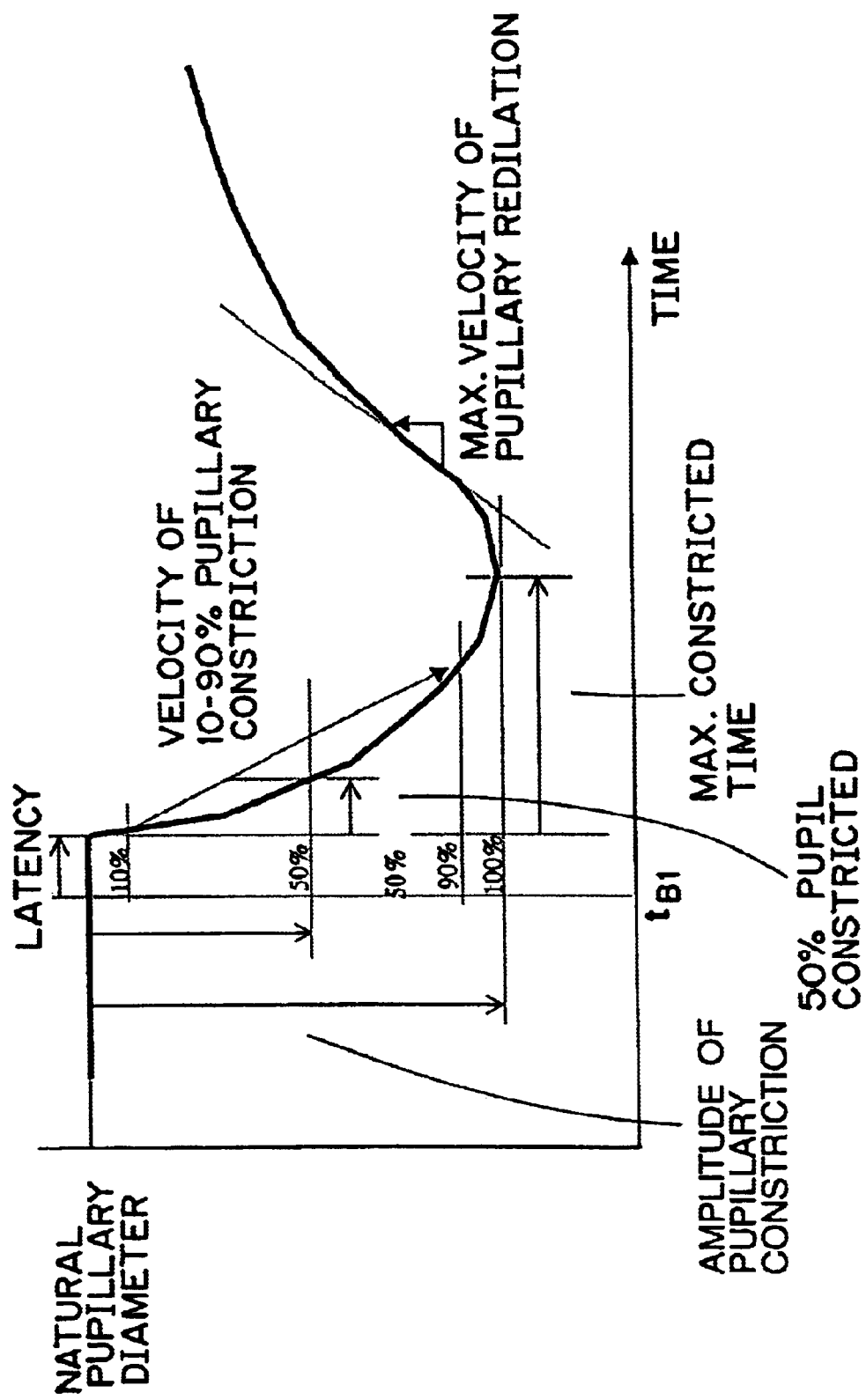
FIG. 7 is a chart showing a change of the pupillary diameter before and after application of the light stimulus in the form of the flash light.

The index calculator 32 of the calculating unit 3 shown in FIG. 1 is operable to calculate the indexes indicative of the pupillary characteristic (either static or dynamic) based on the pupillary change in response to the light stimulus applied. The pupillary characteristic means a quality associated with change in pupillary diameter. FIG. 7 illustrates change of the pupillary diameter before and after application of the light stimulus in the form of the flash light shown in FIG. 2B. Referring to FIG. 7, the indexes indicative of the static or dynamic characteristic of the pupil will be described.

The static characteristic of the pupil refers to the quality of the pupil in a static condition, specifically, the pupillary diameter (hereinafter referred to as "initial pupillary diameter") in a normal state before application of the light stimulus. The initial pupillary diameter is included in the quality associated with "change" in pupillary diameter because there is an index that provides the basis for calculation of the degree of change of the pupil with respect to the criterion represented by the initial pupillary diameter, such as "rate of pupillary constriction" as will be discussed later, and also because the initial pupillary diameter provides an index characteristic of the pupil in a non-stimulated state in which no light stimulus change. On the other hand, the dynamic characteristic of the pupil refers to a quality of the pupil in a dynamic state such as latency, pupillary constriction ratio (=amplitude of pupillary constriction/pupillary diameter in a normal state), velocity of 10–90% pupillary constriction, 50% pupil constricted time, pupillary constriction time, maximum velocity of pupillary redilation, maximum velocity of pupillary constriction and maximum acceleration of pupillary constriction. With reference to FIG. 7, these various indexes will be discussed.

The natural pupillary diameter is defined as meaning the diameter of the pupil measured in a normal state before application of the light stimulus. For this natural pupillary diameter, the diameter of the pupil measured at an arbitrarily chosen timing before application of the light stimulus or an average value of diameters of the pupil measured at arbitrarily chosen time intervals before application of the light stimulus may be equally used. In addition, the diameter of the pupil at an arbitrary timing after application of the light stimulus, but before start of the pupillary constriction or the time-based average value of the pupillary diameters at arbitrary time intervals after application of the light stimulus may be equally employed for the natural pupillary diameter.

The latency refers to a length of time required for the pupil to respond to the light stimulus subsequent to application of the light stimulus to the pupil. As is well known to those skilled in the art, the pupil does not necessarily respond to a light stimulus the exact moment the light stimulus is applied, and has a delay in response. Specifically, this delay is a cumulation of the length of time required for the light stimulus to be photoelectrically converted into electric impulses that are subsequently transmitted to the ophthalmic nerve; the length of time required for secretion of a chemical substance, known as a neurotransmitter, that transmits the nerve impulses across intercellular gaps; the length of time required for the effector to drive the smooth muscle in response to the electric impulses appearing at the centrifugal nerve ending; and so on.

The pupil constricted time refers to the length of time as measured between certain timings during constriction of the pupil taking place in response to the light stimulus. Specifically, the length of time during the pupillary constriction takes place from start to end is referred to as the maximum pupil constricted time. While the difference between the natural pupillary diameter and the pupillary diameter measured at the end of the pupillary constriction is referred to as a total amount of the pupil constricted or an amplitude of pupillary constriction, the length of time required for the pupillary diameter to decrease 50% relative to that measured at the start of the pupillary constriction is referred to as the 50% pupil constricted time. By the same token, 10% and 90% pupil constricted times represent the lengths of time requires for the pupillary diameter to decrease 10% and 90%, respectively, relative to that measured at the start of the pupillary constriction. 10–90% pupil constricted time represents the time span between the timing of 10% constriction of the pupillary diameter and the timing of 90% constriction of the pupillary diameter relative to that measured at the start of the pupillary constriction. Thus, the pupil constricted time used herein is a general term used to encompass various times associated with the pupillary constriction.

The pupillary constriction ratio stands for the ratio of the amplitude of pupillary constriction the amplitude of pupillary constriction divided by the natural pupillary diameter.

The velocity of pupillary constriction, or the pupillary constriction velocity, refers to the amount of change of the amplitude of pupillary constriction per unitary time and can be defined in numerous ways depending on how the unitary time is reckoned. As shown in FIG. 7, the 10–90% pupil constricting velocity stands for the mean velocity of pupillary constriction during a time span between the respective timings at which 10% and 90% decreases have taken place in the pupillary diameter relative to the natural pupillary diameter. The maximum velocity of pupillary constriction means the maximum value of velocity occurring during change of the pupillary diameter upon constriction with passage of time. (See, T. Utsumi, et al., "%Shukudouryou, %Sokudo wo Kuwaeta Atarashii Bunsekihou ni yoru Taihikarihannou no Kenkyu (Studies on Light Response Reaction with New Analyzing Method using % Pupil Constricted Amount and % Velocity)", Japan Ophthalmic Bulletin, Vol. 142, No. 2, pp. 223–228. 1991.) This may be said to be an index indicative of the velocity that is correlated with the maximum velocity of pupillary constriction and the amplitude of pupillary constriction.

The acceleration of pupillary constriction refers to the rate of change of the pupillary constriction velocity per unitary time and can, as is the case with the pupillary constriction velocity, be defined in numerous ways depending on how the unitary time is reckoned. The maximum acceleration of the pupillary constriction therefore refers to the maximum value of acceleration occurring during change of the pupillary diameter upon constriction with passage of time. The length of time necessary to attain the maximum velocity of pupillary constriction refers to the length of time required to attain the maximum velocity of pupillary constriction subsequent to start of the pupillary constriction.

The velocity of pupillary redilation, or the pupillary redilating velocity, refers to the amount of redilation of the pupil, or the pupil redilated amount, per unitary time and can be defined in numerous ways depending on how the unitary time is reckoned. The maximum velocity of pupillary redilation refers to the maximum value of velocity occurring during change of the pupillary diameter upon redilation with passage of time. The length of time necessary to attain the maximum velocity of pupillary redilation refers to the length of time required to attain the maximum velocity of pupillary redilation subsequent to start of the pupillary constriction or redilation whichever chosen as desired. In the illustrated embodiment, the former definition is employed. The % pupil redilating velocity refers to the reverse of, and may be the same as the % pupil constricting velocity and can be obtained by dividing the maximum velocity of pupillary redilation by the amplitude of pupillary constriction. The pupillary redilating velocity used herein is a general term used to encompass those various velocities during redilation that can be specifically defined.

50-50% time interval refers to the length of time that passes from the timing at which the pupil has constricted 50% of the amplitude of pupillary constriction to the timing at which the pupil being redilated returns to the 50% pupil constricted amount. This 50%-50% time interval is an index comprises of a combination of respective indexes indicative of the pupil constricting time, or the time during which pupillary constriction takes place, and the pupil redilating time or the time during which pupillary redilation takes place, respectively.

Referring again to FIG. 1, the database 4 stores indexes which correspond to those indexes described above and which define as reference (hereinafter referred to as "base indexes" the pupillary change of one or more subjects. Where the calculating unit 3 is employed in the form of PC, the database 4 is configured in a storage device such as, for example, a hard disk of such PC. This storage device can store the indexes calculated by the calculating unit 3 and the indexes so stored can be added to the database 4 as new data. This database 4 can also be configured in a database server connected through a network.

The display unit 5 may be an indicator such as a display device and/or a printer. The display unit 5 can provide a visual indication of the indexes associated with the respective pupils of the subject and the other subject. An examiner assigned to conduct the test can ascertain from the display unit 5 that what relative value the subject has shown as compared with the other subject. As the index associated with the pupil of the other subject, it may not be always the index of the other subject, but also an mean value of a plurality of subjects or that of a specific group of subjects. In other words, if the other subject is the one desired to be compared with the subject, any index other than the index of the subject may be employed. Also, as the index of the other subject, the index of the subject obtained in the past may be employed.

The various component parts of the non-invasive brain function examining apparatus 100 have been described above. In the next place, the operation of the non-invasive brain function examining apparatus 100 of the structure hereinabove described will be described. It is to be noted that although various operation of the non-invasive brain function examining apparatus 100 are performed by the various component parts thereof described above, the sequence and overall control of operation of the non-invasive brain function examining apparatus 100 are carried out by a central processing unit (not shown).

Figure 8:
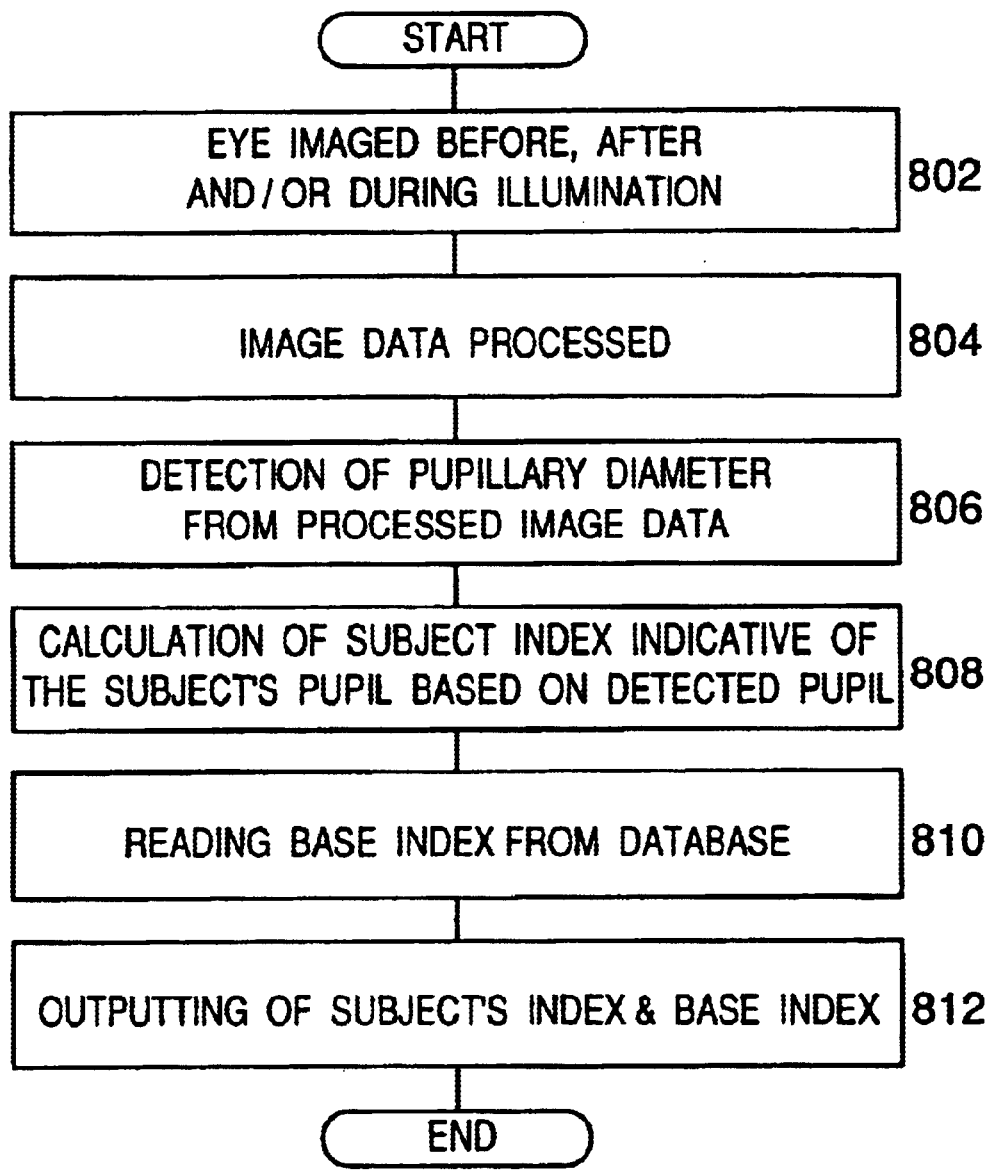
FIG. 8 is a flowchart showing the sequence of operation of the brain function examining apparatus.

FIG. 8 illustrates the flowchart showing the sequence of operation of the non-invasive brain function examining apparatus 100. With the non-invasive brain function examining apparatus 100 electrically powered on, the CCD camera 23 of the imaging unit 2 monitors the subject's eye E (FIG. 1) before, after and/or during illumination with light emitted from the light source 1 (FIG. 1) at step 802. Image data indicative of the subject's eye (FIG. 1) imaged by the CCD camera 23 are outputted from the CCD camera 23 to the image processing unit 30 of the calculating unit 3. The image processing unit 30 (FIG. 1) in response to receipt of the image data from the CCD camera 23 performs a predetermined image processing at step 804. The image processing unit 30 (FIG. 1) outputs the processed image data to the pupillary detector 31 (FIG. 1). In response to receipt of the processed image data from the image processing unit 30 (FIG. 1), the pupillary detector 31 (FIG. 1) detects the pupil at step 806. When the pupil is detected, the pupillary diameter is determined. Based on the pupillary diameter so determined, the index calculator 32 (FIG. 1) calculates the subject indexes indicative of the characteristic of the subject's pupil at step 808. On the other hand, the central processing unit (not shown) of the non-invasive brain function examining apparatus 100 (FIG. 1) reads out from the database 4 (FIG. 1) the index of the other subject what can be used as the base index described above, at step 810. This central processing unit (not shown) outputs the calculated subject index and the base index to the display unit 5 (FIG. 1).

Figure 9:
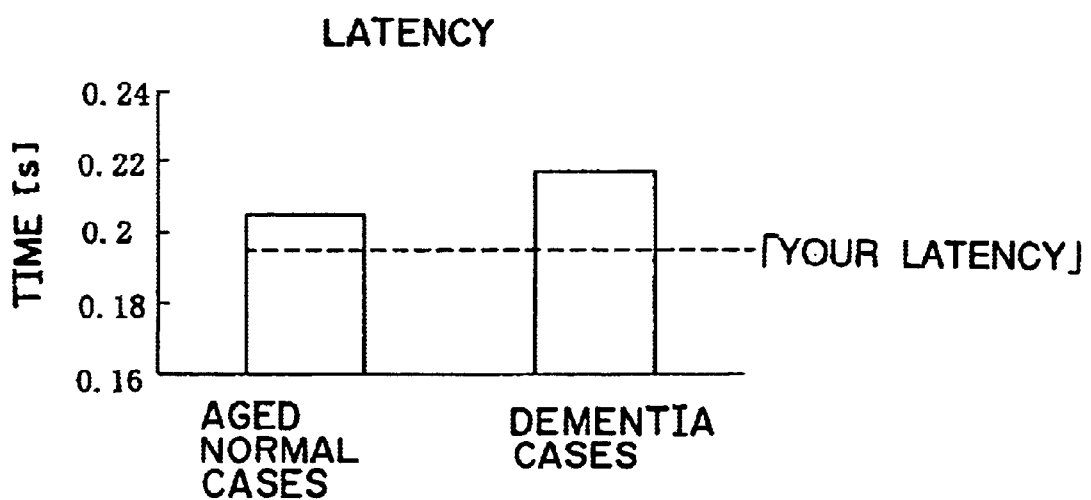
FIG. 9 is a diagram showing a screen display outputted by a display unit when the index is latency.

FIG. 9 illustrates an example of the visual indication displayed by the display unit 5 (FIG. 1) when the index is the latency. As the base index, the mean latency of each of a group of six aged normal cases and a group of six dementia cases is employed and displayed. On the other hand, the latency of the subject is indicated by an ancillary line labeled with the legend "Your Latency". In this way, by displaying the base index and the subject's index in a superimposed fashion, the relative position of the subject as compared with the other subject can be clearly shown. Accordingly, the physician can utilize the relative positional relationship of the respective values of the displayed indexes to determine whether or not the condition of the subject's brain function is similar to that of the dementia case, that is, whether or not the subject is suffering from a suspected dementia or the like. It is to be noted that in the foregoing description the index taken as representing the latency only for the purpose of illustration and any other index can be employed provided that it is any of the foregoing indexes. Also, display may be made by specifying the normal cases according to age and/or sex. Although FIG. 9 is shown in the form of a bar graph, various modes of display are available. Regardless of what method is used to display, any method should be included within the scope of the present invention provided that the position of the subject relative to the other subject can be displayed clearly.

Second Embodiment

In the foregoing embodiment, it has been described that by outputting the subject's index outputted to the display unit 5 and the base index stored in the database 4, the physician can easily determine whether or not the subject may be similar to the index of a group of categories employed as the base indexes. However in the second embodiment which will now be described, description will be made in connection with the non-invasive brain function examining apparatus including a determining unit for automatically determining the condition of the subject's brain function by comparing the subject's index with the base index stored in the database 4.

Figure 10:
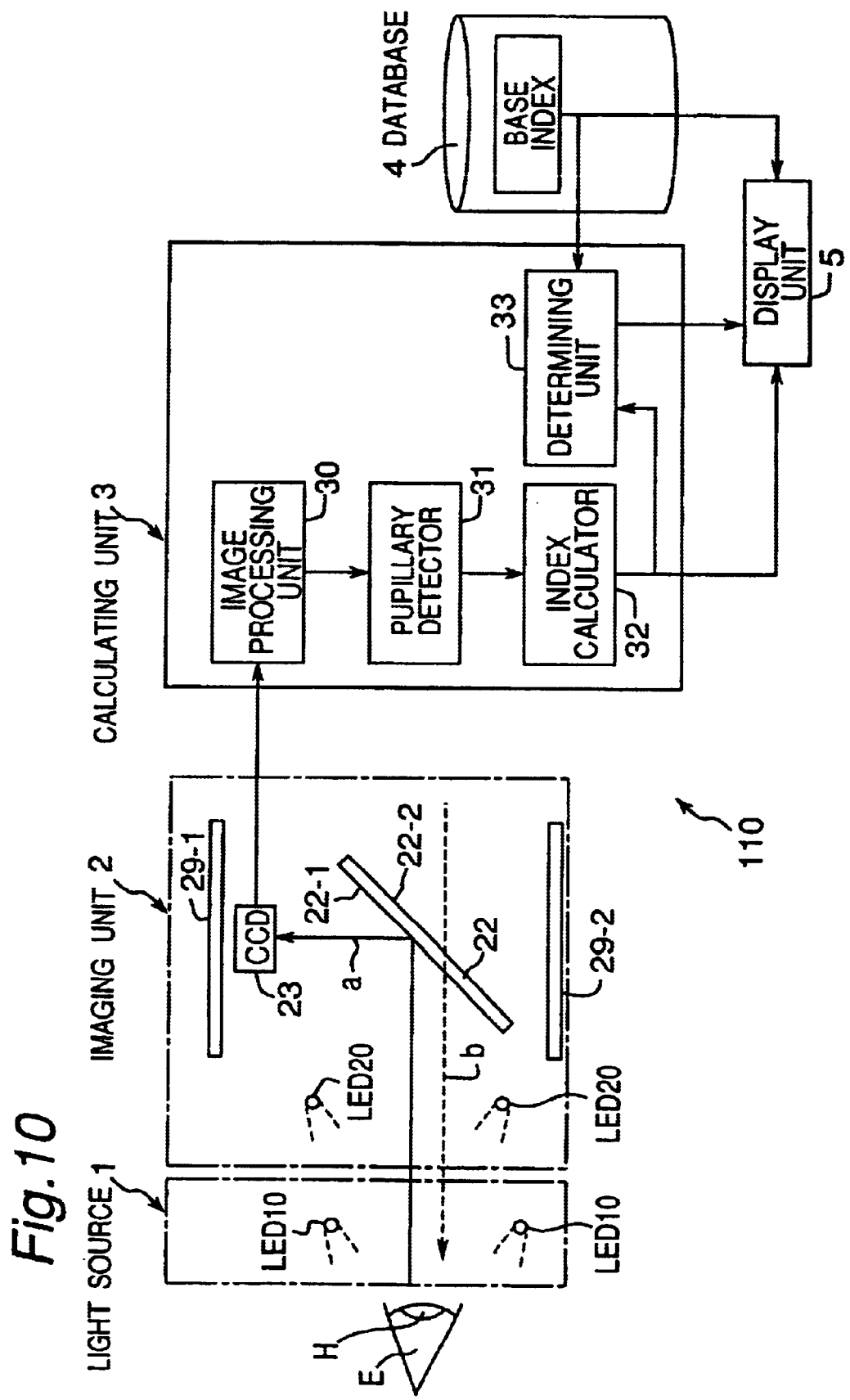
FIG. 10 is a diagram showing the brain function examining apparatus according to a second preferred embodiment of the present invention.

FIG. 10 illustrates the non-invasive brain function examining apparatus 110 according to the second embodiment. The brain function examining apparatus 110 according to the second embodiment differs from the brain function examining apparatus 100 shown in FIG. 1 in that the calculating unit 3 used in the second embodiment of the present invention additionally includes a determining unit 33. Other than the use of the determining unit 33 in the brain function examining apparatus 110 according to the second embodiment, the brain function examining apparatus 110 is similar to the brain function examining apparatus 100 and, therefore, component parts of the brain function examining apparatus 100 that are equally employed in the brain function examining apparatus 110 will not be reiterated for the sake of brevity.

Where the calculating unit 3 is a PC, the determining unit 33 is configured by the utilization of an calculating function thereof. This determining unit 33 formulates, based on the base indexes stored in the database 4, a determining criterion used to determine the brain function. This determining unit 33 receives the indexes that are used for formulation of the determining criterion from the index calculator 32 and the base indexes from the database 4 to formulate the determining criterion. Also, the determining unit 33 compares the subject's and base indexes stored in the database 4 with reference to the determining criterion to determine the brain function of the subject. This determining unit 33 can output a result of determination to the display unit 5.

Hereinafter, the operation of the determining unit 33 can be specifically described. In the following description, the latency is taken as an example of the indexes descriptive of the dynamic characteristic. It is needless to say that any other index can be employed.

The current latency TL obtained from the pupillary light reflex exhibited by the subject and the previous latency TL1 of the same subject that was obtained under the same measuring condition are first compared with each other. The current latency TL may be the value obtained by a single measurement or an average value of data obtained by a series of repeated measurement. The previous latency TL1 may be a value obtained at a certain timing in the past or an average value. Also, it may be an average value of plural data obtained during a certain period in the past with respect to the subject.

If a result of comparison in magnitude between the current latency TL and the previous latency TL1 has indicated that TL−TL1<C1 (wherein C1 is a constant), the subject's brain function is deemed normal, but it will be deemed abnormal if the result of comparison indicates otherwise. It is to be noted that the less-than sign may be replaced with the less-than/equal sign ($\leqq$). It is to be noted that although in the foregoing and following description the constant will be assumed only one value, it may not be limited to a single value, but may be a value within a certain range so that not only can determination of one of alternatives of whether or not the brain function has an abnormality be carried out, but the degree of possibility of presence of an abnormality in the brain function can also be determined.

If a result of comparison in magnitude between the current latency TL and the mean latency TL2 exhibited by a plurality of other normal cases under the same measuring condition has indicated that TL−TL2<C2 (wherein C2 is a constant), the brain function of the subject is determined normal, but if the result of comparison indicates otherwise, it will be deemed that there is a high probability of senescence. It is to be noted that the less-than sign may be replaced with the less-than/equal sign ($\leqq$).

Also, if a result of comparison in magnitude between the current latency TL and the mean latency TL3 exhibited by the plural autonomic disorder cases under the same measuring condition has indicated that TL−TL3<C3 (wherein C3 is a constant), the brain function of the subject is determined normal, but if the result of comparison indicates otherwise, it will be deemed that there is a high probability of autonomic disorder. It is to be noted that the less-than sign may be replaced with the less-than/equal sign ($\leqq$).

In addition, if a result of comparison in magnitude between the current latency TL and the mean latency TL4 exhibited by the plural dementia cases under the same measuring condition has indicated that TL−TL4<C4 (wherein C4 is a constant), the brain function of the subject is determined normal, but if the result of comparison indicates otherwise, it will be deemed that there is a high probability of dementia. It is to be noted that the less-than sign may be replaced with the less-than/equal sign ($\leqq$).

Figure 11:
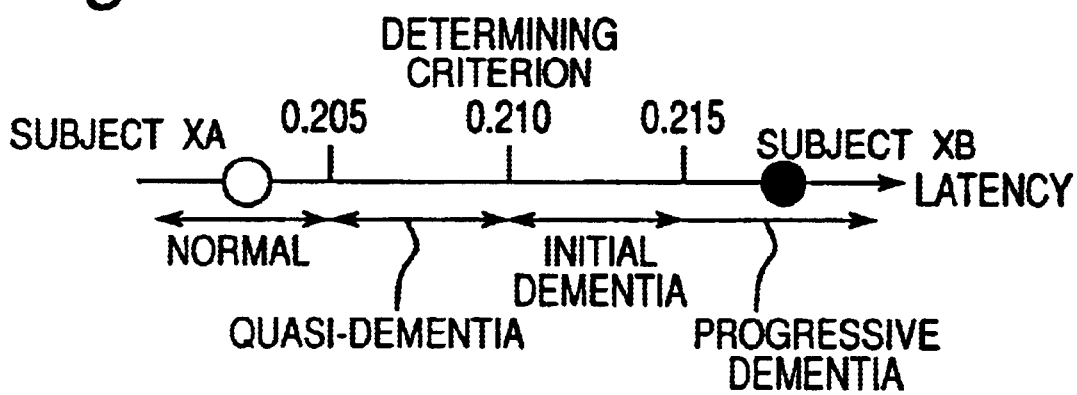
FIG. 11 illustrates an example of a determining criterion that can be used in determining dementia.

Furthermore, if a result of comparison in magnitude between the current latency TL and the mean latency TL5 exhibited by the plural Alzheimer's disease cases under the same measuring condition has indicated that the latency TL−the mean latency TL5<C5 (wherein C5 is a constant), the brain function of the subject is determined normal, but if the result of comparison indicates otherwise, it will be deemed that there is a high probability of Alzheimer's disease. It is to be noted that the less-than sign may be replaced with the less-than/equal sign FIG. 11 illustrates an example of the determining criterion used to determine dementia cases. In this determining criterion, a plurality of conditions of the latency are set and are classified in specific cases which include normal, quasi-dementia, initial dementia and progressive dementia. As far as the example shown in FIG. 11 is concerned, the threshold value between normal and quasi-dementia reads 0.205; the threshold value between quasi-dementia and initial dementia reads 0.210; and the threshold value between initial dementia and progressive dementia reads 0.215.

Figure 12A:
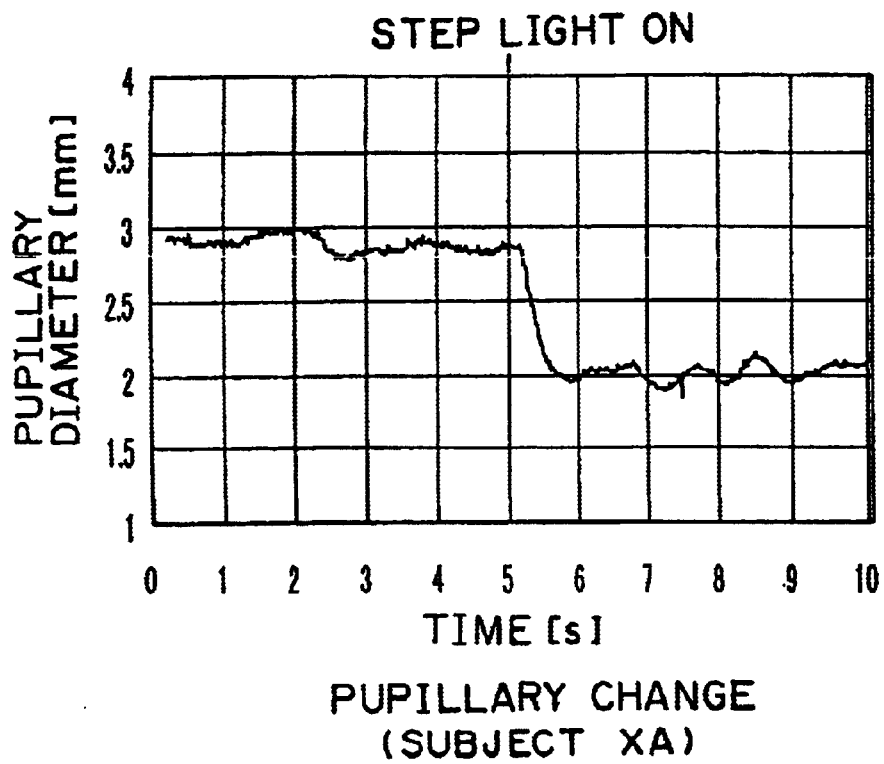
FIG. 12A is a chart showing a change of the pupillary diameter exhibited by a subject XA when measurement is carried out by applying the light stimulus in the form of the step light.
Figure 12B:
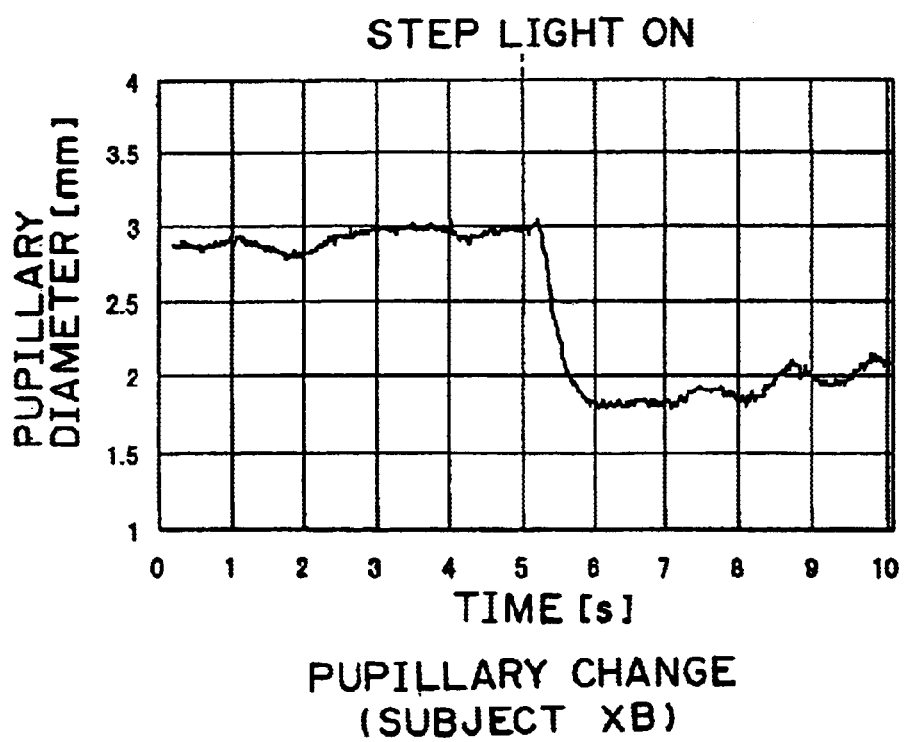
FIG. 12B is a chart showing a change of the pupillary diameter exhibited by a subject XB when measurement is carried out by applying the light stimulus in the form of the step light.

Actually measured examples using the determining criterion so formulated in the manner described above will now be described. FIG. 12A illustrates the pupillary change exhibited by the subject XA exhibited when the light stimulus in the form of the step light is applied. On the other hand, FIG. 12B illustrates the pupillary change exhibited by the subject XB exhibited when the light stimulus in the form of the step light is applied. As discussed hereinbefore, the latency means a period from the start of illumination with light to the timing at which the pupillary fight reflex occurs. As a result of the measurement, the latency of the subject XA was 0.200 and that of the subject XB was 0.217. The determining unit 33 (FIG. 10) compares those result of measurement with the determining criterion (FIG. 11) and outputs respective results of determination that the subject XA is normal (as indicated by ○ in FIG. 11) and that the subject XB is suffering from progressive dementia (as indicated by ● in FIG. 11). Since the respective results of actual measurement was that the subject XA was normal and the subject XB was suffering progressive dementia, the results of measurement conducted according to this embodiment of the present invention may be deemed correct. Although in the example shown in FIG. 11, the index used for determination is only the latency, two or more indexes may be employed for the determination.

In order for the determining unit 33 (FIG. 10) to formulate the determining criterion (FIG. 11), it is preferred to use measurement data associated with the latencies of normal and dementia cases. If the determining criterion is formulated based on the many measurement data, an average value of cases to be determined can be comprehended and more accurate determination will be possible. FIG. 13 illustrates an example of the determining criterion formulated. The bars shown in the bar graph of FIG. 13 represent respective average latencies exhibited by a group of 10 aged normal cases and a group of 6 dementia cases with respect to step light. Average ages of cases of the respective groups were the same. The threshold values for classifying the results of determinations are so set that as shown in FIG. 13, the determining unit 33 can determine that if the latency is smaller than the average value of the aged normal cases the subject is normal; if the latency is greater than the average value of the aged normal cases, but the difference between the average value of the aged normal cases and the latency is smaller than half the difference between the dementia cases and the aged normal case, the subject is deemed suffering from quasi-dementia; if the latency is smaller than the average value of the dementia cases, but the difference thereof is greater than half the difference between the dementia cases and the aged normal cases, the subject is deemed suffering from initial dementia; and if the latency is greater than the average value of the dementia cases, the subject is deemed suffering from progressive dementia. The number of cases to be determined may not be limited to four, but may be more than four. Also, the threshold values so set may not be limited to those shown in FIG. 13. Also, each of the threshold values may not be limited to a single value, but may be a value within a certain range. The cases to be classified may also not be limited to those discussed above. The method of formulating the determining criterion described above may not be limited to that associated with the latency, but may include those associated with the other indexed. However, the orientation of the sign of inequality may vary depending on the particular index.

FIGS. 14A to 14F illustrate examples of results of measurement for formulation of the determining criterions of each of some of the indexes. Subjects tested in connection with FIGS. 14A to 14F include a group of 8 young normal cases, a group of 20 aged normal cases, a group of 13 cerebrovascular dementia (CVD) cases and a group of Alzheimer-type dementia (SDAT/AD) cases and, thus, 19 persons in four groups. The light stimulus employed is a flash light emitted for 100 msec. Bars in the respective bar graphs of FIGS. 14A to 14F represent an average value, and a symbol "I" in each bar represents the error tolerance defined by 2 times the standard deviation.

According to the graph shown in FIG. 14A that is related to the latency, the aged normal cases have shown a latency greater than that of the young normal cases, but the latency of each of the cerebrovascular dementia cases and Alzheimer-type dementia cases is slightly greater than that of the aged normal cases. According to the graph shown in FIG. 14B that is related to the pupillary constriction time, although there is a difference between the young normal cases and the other cases, virtually no difference is found among the aged normal cases, the cerebrovascular dementia cases and the Alzheimer-type dementia cases. According to the graph of FIG. 14C related to the pupillary constriction rate, the pupillary constriction rate exhibited by the Alzheimer-type dementia cases is lower than that of the other cases. As far as the maximum acceleration of pupillary constriction shown in FIG. 14D, the maximum velocity of pupillary constriction shown in FIG. 14E and the maximum velocity of pupillary redilation are concerned, substantially similar tendencies have been shown. In other words, the young normal cases have exhibited the largest value, followed by that of the aged normal cases. The cerebrovascular dementia cases and the Alzheimer-type dementia cases have shown respective values similar to each other.

With respect to the results shown respectively in FIGS. 14A to 14F, it is easy to formulate the determining criterion (shown in FIG. 11) which has been described in connection with the latency. It is to be noted that the respective results shown in FIGS. 14A to 14F are subject to variation depending on the condition of the light stimulus which is one of the measuring conditions and, therefore, it is preferred to consolidate for each of the measurement results.

While in FIGS. 11 and 13, the method of formulating the determining criterion and the determining method both associated with the single index, it is possible to formulate the determining criterion when the plural indexes are taken into consideration. In such case, it is possible to formulate a number of determining criterions depending on the combination of the plural indexes.

Figure 15A:
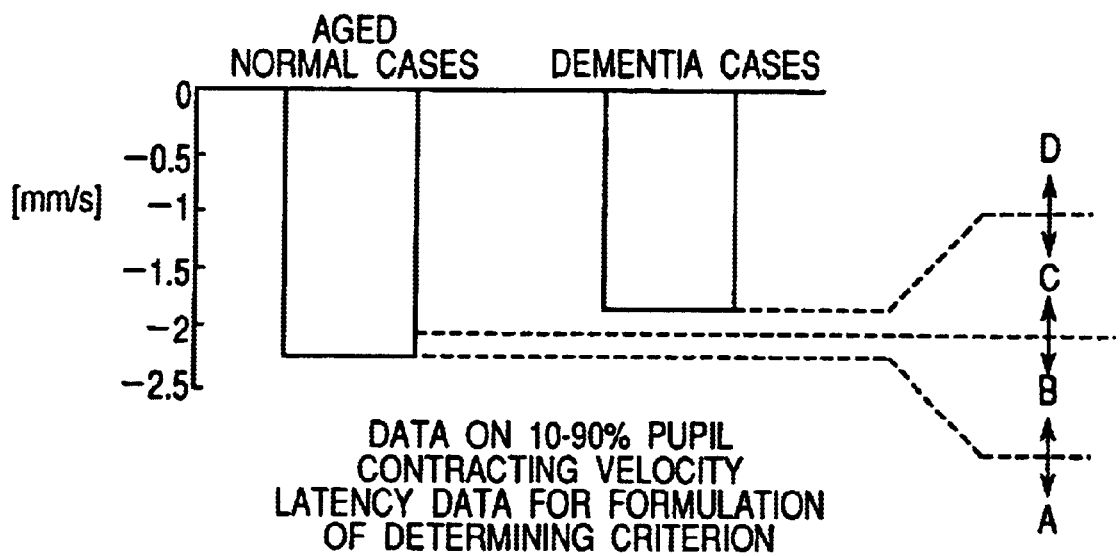
FIG. 15A illustrates an example of the determining criterion associated with the 10–90% pupil constricting velocity.
Figure 15B:
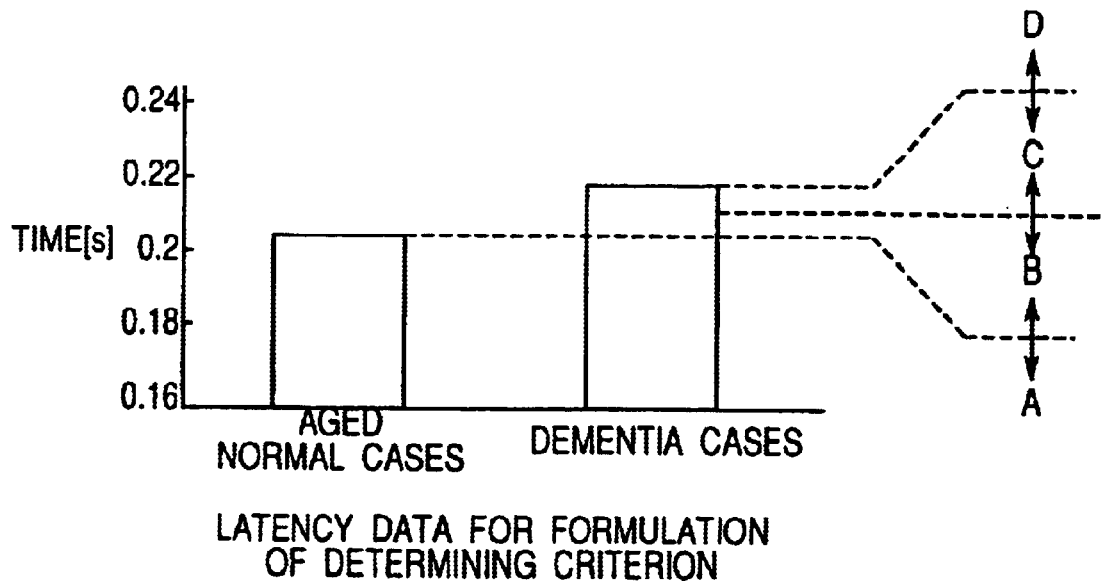
FIG. 15B illustrates an example of the determining criterion associated with the latency.

Hereinafter, the method of formulating the determining criterions using the two indexes will be described. For the two indexes, the 10–90% pupillary constricting velocity and the latency are taken into consideration. FIG. 15A illustrates an example of formulation of the determining criterion associated with the latency. For each indexes, the respective threshold value is set in a manner similar to that for the single index. In FIGS. 15A and 15B, the respective threshold values are so set that each of the indexes can be classified into A to D. Then, the determining criterion is formulated by combining these indexes. Here, the two determining criterions are envisioned. With respect to these two determining criterions, which one of them is optimum cannot be generally determined and should therefore be selected suitably. By way of example, when formulating the severe determining criterions, such a determining criterion should be so formulated that only when the two indexes are classified into D dementia can be diagnosed. In contrast, where a moderate determining criterion is to be formulated, such a determining criterion should be so formulated that only when at least one of the two indexes is classified into D, dementia can be diagnosed. In the case of the severe determining criterion, it may be possible that the rate of pseudo-positive cases in which the subject not suffering from dementia may be diagnosed as suffering from dementia may increase. On the other hand, in the case of the moderate determining criterion, it may be possible that the rage of pseudo negative cases in which the subject suffering from dementia may be diagnosed as suffering from no dementia.

The method of formulating the determining criterions associated with the two indexes shown in FIGS. 15A and 15B, respectively, may not be limited to the above described severe and moderate determining criterions. In other words, various combination of the classes A to D of each of the indexes may be contemplated and the number of determining criterions corresponding to the number of the combination can be formulated. The use of those determining criterions should not be construed as departing from the scope of the present invention.

Figure 16A:
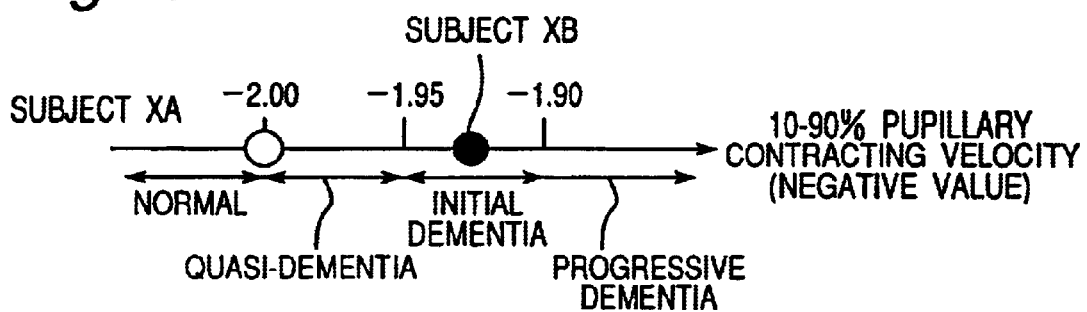
FIGS. 16A and 16B illustrate different determining criterions formulated by the use of two indexes, i.e., 10–90% pupil constricting velocity and the latency, respectively.
Figure 16B:
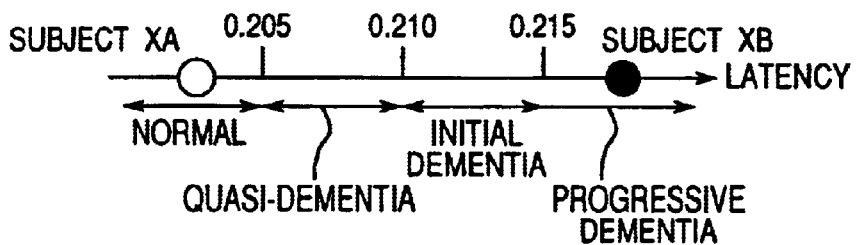

FIGS. 16A and 16B illustrates the respective determining criterions formulated using two indexes, i.e., the 10–90% pupillary constricting velocity (FIG. 15A) and the latency (FIG. 15B). The subjects are XA and XB, and results of measurement of their pupillary diameters are shown in FIGS. 12A and 12B. As a result of measurement, the 10–90% pupillary constricting velocity and the latency of the subject XA were −2.00 mm/s and 0.200 s, respectively. On the other hand the 10–90% pupillary constricting velocity and the latency of the subject XB were −1.93 mm/s and 0.217 s, respectively. Although if based on the determining criterion (FIG. 16A) of the 10–90% pupillary constricting velocity the subject XB may be diagnosed as suffering from initial dementia, he or she may be diagnosed as suffering from progressive dementia if based on the determining criterion (FIG. 16B) of the latency. In reality, however, the subject XB has suffered from rather progressive dementia. In this case, the accurate result of diagnosis can be obtained if the determining criterion of the latency is relied on. However, whichever one of the determining criterions is used, the result would be obtained that the subject is possibly suffering from dementia rather than healthy normal and can be used by a physician for reference purpose.

In the foregoing, the determining unit 33 (FIG. 10) has been described as performing procedures for formulating the determining criterions. The determining unit 33 (FIG. 10) can perform all of the procedures associated with the formulation of the determining criterions described above, that is, analysis of the measured data which will eventually becomes the indexes and formulation of the determining criterions. While in the foregoing examination of dementia as one of the examination items on the brain function has been discussed in detail, a similar description equally applies to diagnosis of the degree of senescence, the degree of autonomic function, or the Alzheimer's disease (or the Alzheimer-type dementia).

Third Embodiment

It has been described that according to the first embodiment of the present invention, by outputting the subject's index outputted to the display unit 5 and the base index stored in the database, the physician can easily determine if the subject is similar to the indexes of the group of categories employed as the base index. In the third embodiment, however, the brain function examining apparatus including a multivalue calculator will be described. The multivalue calculator is provided for converting the plural indexes into different values (discriminant scores) smaller in number than the number of the plural indexes to thereby reduce the amount of data to be handled.

FIG. 17 illustrates the brain function examining apparatus 120 according to the third embodiment. This brain function examining apparatus 120 differs from the brain function examining apparatus 100 (FIG. 1) of the first embodiment in that in the third embodiment a multivalue calculator 34 is added to the calculating unit 3. Other component parts than the multivalue calculator 34 and components specifically referred to are substantially similar to those employed in the brain function examining apparatus 100 (FIG. 1) and are not therefore reiterated for the sake of brevity.

Before the description of the multivalue calculator 34 proceeds, the database 4 stores all necessary information including information DA including information associated with the subject and the measurement environment both necessary for the brain function examination, such as indexes indicative of individual variables associated with the pupillary change; discriminant scores that can be obtained as a result of calculation performed by the multivalue calculator 34 based on the indexes; environmental conditions of the subject and other subjects such as age, sex, history of diseases, current disease, date and place of measurement, brightness and temperature or the like of the place of measurement, result of intelligence tests and so on. In this embodiment, data such as the pupillary indexes of the subject, the discriminant score and the information DA including information associated with the subject and measurement environment can be registered in the database 4. By causing the database 4 to accumulate those data, the highly reliable database accumulating as many subject data as possible therein can be configured. It is to be noted that in this embodiment the database 4 can be implemented by the same PC as that containing the index calculator 32 and the multivalue calculator 34, but may not be always limited thereto.

The display unit 5 may be an indicator such as a display device and/or a printer. The display unit 5 can provide a visual indication of a discriminant score w1 of the subject and a discriminant score w2 of the other subject so that one can ascertain what value the discriminant score w1 of the subject takes relatively as compared with the discriminant score w2 of the other subject. For the discriminant score w2 of the other subject, it may be either a single discriminant score of the other subject or an average value of respective discriminant scores of the plural other subjects or an average value of discriminant scores of a particular group of subjects. In other words, where the subject is the one desired to compared with such subject, any value other than the discriminant score of such subject can be employed. Also, for the pupillary index of the other subject, it may be a discriminant score of such subject obtained in the past. Although now shown in FIG. 1, the display unit 5 can display not only the discriminant scores w1 and w2, but also the pupillary index and any other data such as described above.

The multivalue calculator 34 selects a discriminant score based on the various pupillary indexes by the utilization of a discrimination analysis technique in the multivariate analysis. Although it is often that the number of this discriminant score is one, but may be plural. By way of example, by classifying the indexes into a certain number of groups and determining the single discriminant score for each group, it is consequently possible to determine the plural discriminant score based on the entire indexed. In this embodiment, the number of the discriminant score is assumed to be one. The discrimination analysis of the multivariate analysis is to consolidate information on the plural indexes to convert it into one discriminant score and to perform a certain analysis (determination) using such discriminant score. As another multivariate analysis technique, a principal component analysis is known. This is to convert the plural indexes into a number of indexes which is smaller than the number of the plural indexes to thereby consolidate the original many indexes into as small information as possible. It may be said that a pre-processing other than determination of the previously described discrimination analysis technique is generalized. By converting as small the number of indexes as possible, targets to be handled can be reduced to enhance a high speed processing. It is to be noted that the multivalue calculator 34 may, if the calculating unit 3 is in the form of a PC, be configured using the calculating function thereof. However, separate devices may be employed. By way of example, not a personal computer, but a DSP (digital signal processor) or a microcomputer may be employed to configure it.

In the following description of this embodiment, a method of introducing the discriminant score based on the discrimination analysis technique will be described. Needless to say, the first principal component or plural principal component in the principal component analysis technique can be employed as a representative value in place of the discriminant score employed in this embodiment and, therefore, the present invention is not limited to such embodiment. For the details of the multivariate analysis technique, reference may be made to "Igaku Toukeigaku Handobukku (Handbook of Medical Statistics)", edited by H. Miyahara, et al. and published in 1995 from Asakura Shoten; "Tahenryo Dehta Kaiseki Nyumon (Introduction to Multivalue Data Analysis)" by T. Sugiyama and published in 1983 from Asakura Shoten; and "Hisenkei Tahenryo Kaiseki— Nyurarunetto-niyoru Apurohti (Non-linear Multivariate Analysis—Approach by Neural Network)" published in 1996 from Asakura Shoten.

The multivalue calculator 34 applies a discrimination analysis technique of the multivariate analysis to the plural indexes indicative of the characteristic of the pupil H of the subject calculated by the index calculator 32 to thereby calculate a discriminant score representative of as small the indexes as possible. The multivalue calculator 34 also applies the discrimination analysis technique of the multivariate analysis to the plural indexes stored in the database 4 to thereby calculate the discriminant score w2 of the plural subjects.

As hereinabove described, in this embodiment, a single discriminant score is calculated from the plural indexes. Hereinafter, description will be made as to what value each of the discriminant scores w1 and w2 is.

Figures 18A, 18B:
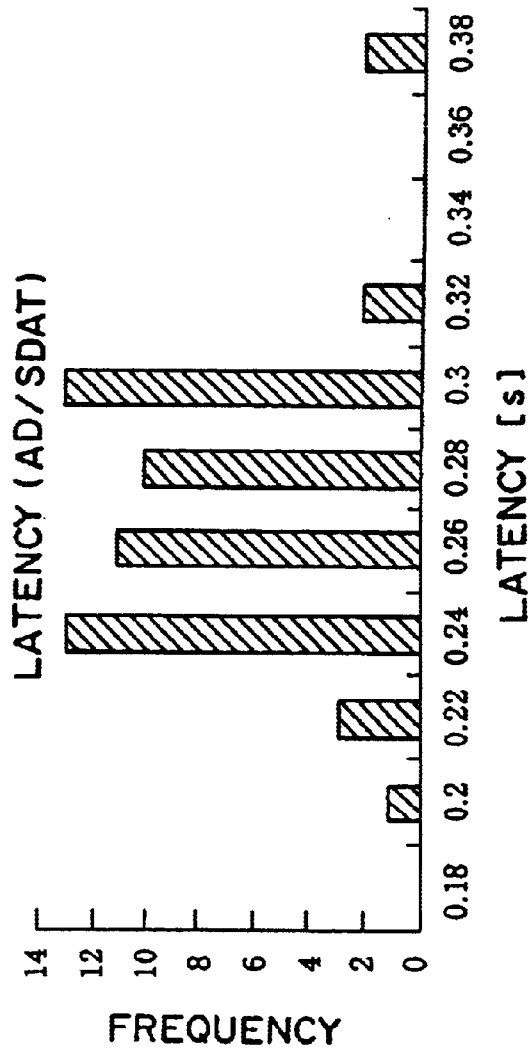
FIG. 18A is a histogram of the latency exhibited by an aged normal case.
FIG. 18B is a histogram of the latency exhibited by an AD/SDAT case.

FIG. 18A illustrates a histogram of the latencies of 57 aged normal cases while FIG. 18B illustrates a histogram of the latencies of 55 Alzheimer-type dementia (AD/SDAT) cases. The average age of a group of the aged normal cases is 74.7 with a standard deviation of 8.40 years whereas the average age of a group of the AD/SDAT cases is 77.1 with a standard deviation of 9.24 years. No statistically significant difference is found between the average ages of the respective groups (p value: p=0.167). Although a statistically significant difference is found between the average latencies of the respective groups (p=0.0011), as shown in FIGS. 18A and 18B, it will readily be understood that the histograms of the respective groups has a considerable overlap. Table 1 below illustrates relations between mean values of the respective groups in connection with the indexes including the latencies and values of the statically significant levels associated with the mean value of each indexes of the respective groups.

TABLE 1

|  | Comparison of Average Values of Aged Normal Group and AD/SDAT Group | p Value |
|---|---|---|
| Latency | Normal < AD/SDAT | 0.0011 |
| Max. Pupillary Constricting Time | Normal > AD/SDAT | 0.274 |
| 50% Pupillary Constricting Time | Normal > AD/SDAT | 0.0689 |
| 50%-50% Time Interval | Normal > AD/SDAT | 0.329 |
| Time Required to Attain Max. Velocity of Pupillary Constriction | Normal > AD/SDAT | 0.0101 |
| Time Required to Attain Max. Velocity of Pupillary Redilation | Normal > AD/SDAT | 0.0675 |
| Time Required to Attain Max. Acceleration of Pupillary Constriction | Normal > AD/SDAT | 0.0006 |
| Natural Pupillary Diameter | Normal > AD/SDAT | 0.0005 |
| Amplitude of Pupillary Constriction | Normal > AD/SDAT | 0.0002 |
| Pupil Constricting Rate | Normal > AD/SDAT | 0.0461 |
| Max. Velocity of Pupillary Constriction | Normal > AD/SDAT | 0.0006 |
| Max. Velocity of Pupillary Redilation | Normal > AD/SDAT | 0.0012 |
| Max. Acceleration of Pupillary Constriction | Normal > AD/SDAT | 0.00606 |
| % Pupillary Constricting Velocity | Normal < AD/SDAT | 0.195 |
| % Pupillary Redilating Velocity | Normal < AD/SDAT | 0.426 |

Generally in carrying out a significant test, it is often that when the p value thereof is below 0.01 or 0.05, it is deemed significant. As shown in Table 1, if 0.05 is taken as a threshold value against the p value, a statically significant difference could be found between the group of the aged normal cases and the group of the AD/SDAT cases with respect to the latency, the time required to attain the maximum velocity of pupillary constriction, the time required to attain the maximum acceleration of pupillary constriction, the natural pupillary diameter, the amplitude of pupillary constriction, the pupil constricting rate, the maximum velocity of pupillary constriction and the maximum velocity of pupillary redilation. Of them, the index resulting in the most statistically significant difference is when the p value is 0.0002 of the amplitude of pupillary constriction. When the number of the subject is fixed, the smaller the p value, the more considerable the difference between the groups, and therefore, when discussing the difference between the groups, the p value is considered in the following description as an index indicative of the magnitude of the difference.

An object of the present invention is to lead out such a value that results in as small the p value as possible by combining some indexes. As hereinbefore described, the smaller the p value, the more considerable the difference, and therefore, it may be expected that the accuracy of determination of which one of the group a certain arbitrary subject belongs to can be increased. Also, not only is a determination to provide a clear distinction such as determination of which one of the group of the normal cases and the group of the AD/SDAT cases the subject belongs to, but a future possible onset of a disease may be foreseen by knowing a result as a continuous quantity indicative of which one of the groups it is close to and how far it is. In this way, any countermeasures can be thought of by implementing a countermeasure.

Figure 19:
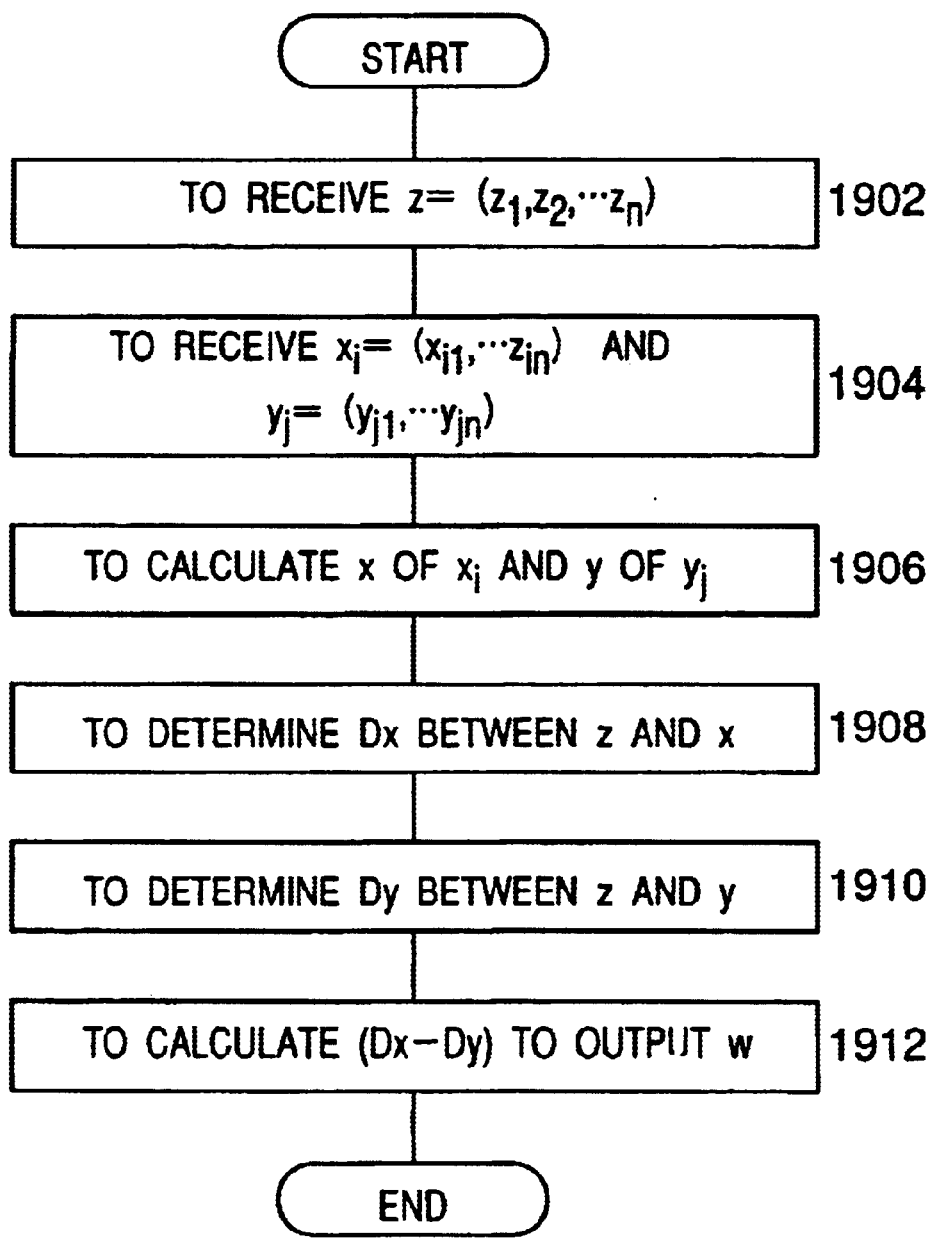
FIG. 19 is a flowchart showing the sequence of calculating a discriminant score w.

FIG. 19 illustrates a flowchart showing the sequence of calculation of the discriminant score w. The multivalue calculator 37 (FIG. 17) first receives a subject index group $z=(z_1, z_2, \ldots, Z_n)$ of a certain subject from the index calculator 32 (FIG. 17) or the database 4 at step 1902. $z_1$ or the like represents the value of each index. The multivalue calculator 34 makes use of, for example, the latency, the natural pupillary diameter, the amplitude of pupillary constriction, the maximum velocity of pupillary redilation, the maximum velocity of pupillary constriction, the time required to attain the maximum velocity of pupillary constriction and the time required to attain the maximum acceleration of pupillary constriction as indexes. Then, the multivalue calculator 34 (FIG. 7) receives a base index group $x_i=(x_{i1}, \ldots, Z_{in})$ of a normal subject and a base index group $y_i=(y_{j1}, \ldots, y_{in})$ of an non-normal subject from the database 4 (FIG. 17) at step 1904, wherein i and j=1, 2, ..., and the multivalue calculator 34 receives base index groups of the plural normal and non-normal persons. These $x_{i1}$ and $y_{i1}$ or the like are a value of each index of the normal person i and the non-normal person j and are the same index as the index used as the subject index. Then, an average index group x of the base index group $x_i$ of the normal persons and an average index group y of the base index group $y_j$ of the non-normal persons are calculated at step 1906. The average index group x means an average value of the normal persons for each index. After calculation of the average index group x, the Maharanobis square distance Dx between the subject index group z and the average index group x is determined at step 1908.

The Maharanobis square distance can be obtained as $Dx=(z-x)A^-(z-x)^T$ by determining the variance and covariance matrices A of the base index group $x_i$, wherein $A^1$ stands for an inverse matrix of A and $(z-x)^T$ stands for the transpose of (z–x). Similarly, the Maharanobis square distance Dy between the subject index group z and the average index group y is determined at step 1910. Finally, (Dx–DY) is calculated to output the discriminant score w at step 1912. By this sequence, the discriminant score can be determined based on the subject index group and the base index group.

Figure 20A:
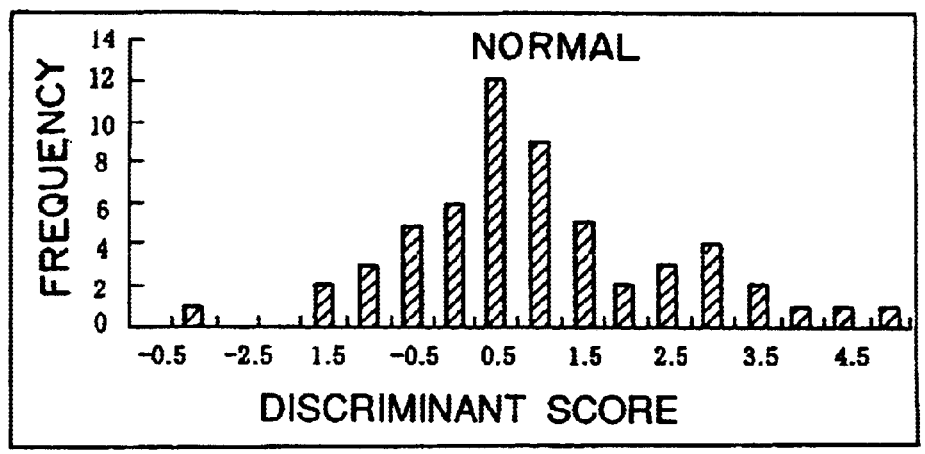
FIG. 20A is a diagram showing the discriminant score w of the normal case and a distribution of frequencies of a person applicable with such discriminant score.
Figure 20B:
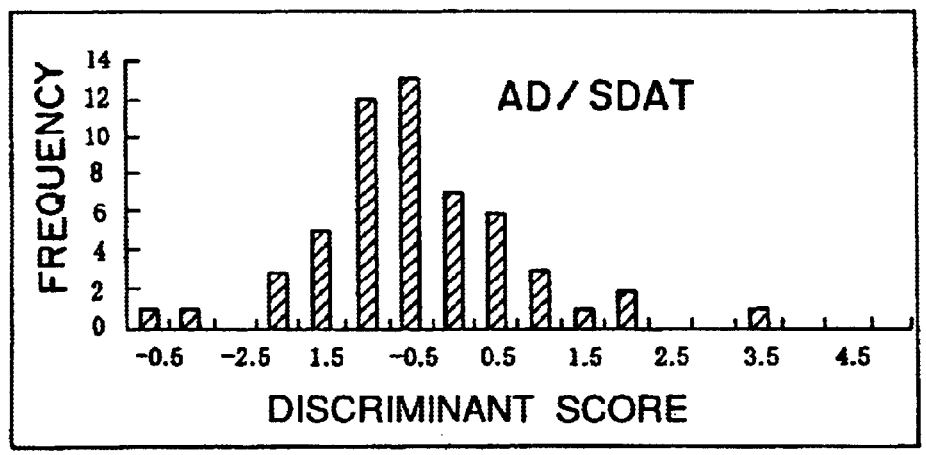
FIG. 20B is a diagram showing the discriminant score w of the AD/SDAT case and a distribution of frequencies of a person applicable with such discriminant score.

Hereafter, the manner of determining the possibility of which one of the normal and non-normal cases the subject belongs to using the discriminant score will be described. Out from the group of the 57 aged normal cases (X) and the group of the 55 Ad/SDAT cases (Y), a subject XC who is evident as to the group to which he or she belongs is sampled. Based on the index of this subject XC and the respective base indexes of each of those groups (X) and (Y), the discriminant score w is calculated. In this instance, the index of the subject XC is the subject index z (FIG. 19). The foregoing procedure is repeated with respect to all of the cases and the histogram of the discriminant scores w is outputted at the display unit 5. By way of example, a display is made on a monitor screen for each of the aged normal group (X) and the AD/SDAT group (Y). FIG. 20A illustrates the discriminant scores w for the aged normal cases and a pattern of frequencies of subjects who have resulted in the discriminant scores. FIG. 20B illustrates the discriminant scores w for the AD/SDAT cases and a pattern of frequencies of subjects who have resulted in the discriminant scores.

The p value indicative of the difference in average discriminant score so determined is 3.82×10-7 and it will readily be seen that this p value is smaller than that of each of the indexes shown in Table 1. In this way, by consolidating some indexes into a single value, decision can be made easily since it is possible to increase the significant difference between the groups (X) and (Y) and also to reduce the number of pieces of the information outputted (in this case the graphs of FIGS. 20A and 20B).

Although in FIGS. 20A and 20B only the discriminant scores w for the aged normal group (X) and the AD/SDAT group (Y), by overlapping the discriminant score for the subject on the graph, a physician, for example, can ascertain which one of the groups (X) and (Y) the subject is near to. The equation for defining the discriminant score for the subject can be expressed as follows:

w=1475−15.175×(Latency)+0.661×(Natural Pupillary Diameter)+2.652×(Amplitude of Pupillary Constriction)+0.618×(Maximum Velocity of Pupillary Constriction)+0.215×(Maximum Velocity of Pupillary Redilation)+0.025×(Maximum Acceleration of Pupillary Constriction)−14.404×(Time Required to Attain Maximum Velocity of Pupillary Constriction)+27.83× (Time Required to Attain Maximum Acceleration of Pupillary Constriction)

Since the variance and covariance matrixes of the indexes taken into consideration are equal between the groups (X) and (Y), the equation for determining the discriminant score can be expressed by a first order linear conjunction of each of the indexes. This equation is generally referred to as a discriminant equation or a discriminant function. For simplicity purpose, whether or not the variance and covariance matrixes are assumed to be equal to each other may be suitably determined depending on the group of cases to be examined.

Although the bar graphs are shown respectively in FIGS. 20A and 20B, display examples of the display unit 5 are only for the purpose of illustration and various manner of display exist. In any event, whatever the manner of display is employed, any method may be employed provided that the position of the subject relative to the other subject can be displayed and the present invention may not therefore be limited thereto.

Fourth Embodiment

In the foregoing third embodiment, the brain function examining apparatus has been described in which by causing the position of the subject relative to the other subjects to be displayed through the display unit 5 in a readily understandable manner based on the discriminant score w, the physician or the like can determine the brain function of the subject. However, in the embodiment which will now be described, the brain function examining apparatus of a type in which the brain function examining apparatus 120 (FIG. 17) is added with the determining unit for automatically determining the condition of the brain function of the subject by comparing the subject index with the base index stored in the database, will now be described.

FIG. 21 illustrates the brain function examining apparatus 130 according to the fourth embodiment of the present invention. The brain function examining apparatus 130 differs from the brain function examining apparatus 120 (FIG. 17) in that in the apparatus 130 a determining unit 33 is added to the calculating unit 3. Other component parts of the brain function examining apparatus 130 except for the determining unit 33 are substantially similar to those employed in the brain function examining apparatus 120 (FIG. 17) and are not therefore reiterated for the sake of brevity.

The determining unit 35 formulates a determining criterion based on the base indexes obtainable from the database 4. The determining criterion is a cue for determination of the brain function. By comparing the discriminant score w1 of the subject with the discriminant score w2 stored in the database 4, and based on the determining criterion, the brain function of the subject is determined.

As shown in FIGS. 20A and 20B, with the determining criterion represented by 0 in the pattern of frequencies for the aged normal group and the AD/SDAT group so determined as hereinbefore described, if the discriminant score w1 is larger than 0, it is deemed normal, but if the discriminant score w1 is smaller than 0, it is deemed dementia. The result of determination is displayed through the display unit 5. The display device in this case may be a display device and/or a printer. It is also possible to output the result of determination in the form of an audio information. By way of example, when the audio information is issued, it is deemed dementia (AD/SDAT), but when no audio information is issued, it is deemed normal.

The value of the determining criterion may not be always limited to 0, but the determining criterion should take a negative value if the rate of erroneous determination which the normal subject may be diagnosed as suffering from dementia, that is, a quasi-positive rate is desired to be reduced. Thus, the determining criterion is variable depending on the requirements. Automatic examination is possible if the determining criterion is predefined and the determining unit 35 performs comparison between the criterion and the discriminant score.

Although in the foregoing Alzheimer-type dementia (including the Alzheimer's disease) was taken into consideration as one of brain disorders, the degree of senescence of the brain function, the degree of autonomic function or dementia such as cerebrovascular dementia or the like can be equally examined and determined.

The inventors of the present invention believe it possible to discriminate young and aged normal cases and case with cerebrovascular dementia and Alzheimer-type dementia in view of the fact that the latency exhibited by the cerebrovascular dementia and Alzheimer-type dementia cases is slightly greater than that exhibited by the aged normal cases and by the utilization of the maximum velocity of pupillary constriction. The inventors of the present invention also believe that also as far as the maximum pupillary constricting time is concerned a significant difference can be found between the young normal cases and the other subject groups, virtually no difference is found between the aged normal cases and the cases with cerebrovascular and Alzheimer-type dementia cases. Accordingly, it is possible to discriminate the cerebrovascular dementia cases based on those indexes (See the Japanese Patent Application No. 2000-047011). With respect to the relation between the degree of senescence and the autonomic nervous system, reference may be made to Ishikawa, et al., "Fukyuu-gata Denshi Doukoukei Irisukohda (C-2514) ni Tsuite (On Handy Electronic Pupil Meter Iriscorder (C-2514))", (Shinkei Ganka (Neuro-Ophthalmology), Vol. 10, No. 2, pp. 106–110, 1993).

In any one of the third and fourth embodiments described hereinbefore, the pupillary index employed by the multi-value calculator 34 may additionally include one or a combination of the pupillary constricting time and the pupillary redilating time.

Fifth Embodiment

In this embodiment, modified forms of the light source 1 and the imaging unit 2, respectively, of the brain function examining apparatus 100 (FIG. 1) will be described. More specifically, the bundle of rays of light projected from the light source towards the pupil has a diameter smaller than the pupillary diameter. Also, it is so constructed that even though the eye motion and the head motion take place, the light will not divert and will travel towards the pupil. In the following description, a device having a unified function of the light source 1 and the imaging unit 2 of the brain function examining apparatus 100 (FIG. 1), that is, a device for measuring the pupillary light reflex will be referred to as a "pupillary measuring device".

FIG. 22 illustrates a schematic diagram showing the brain function examining apparatus 140 including the pupillary measuring device 6 according to this fifth embodiment of the present invention, which is viewed from above. The brain function examining apparatus 140 includes the pupillary measuring device 6, the lighting control unit 7, the calculating unit 3, the database 4 and the display unit 5. Component parts similar to the component parts and functions which have already discussed are shown by like reference numerals. In the following description, the pupillary measuring device 6 and the lighting control unit 7 are described and an additional function of the calculating unit 3 associated therewith is also described. Other functions and structures of the calculating unit 3 are substantially identical with those in the first embodiment of the present invention and are not therefore reiterated for the sake of brevity. Before the specific structure and function of the pupillary measuring device 6 are described, the prior art pupillary measuring devices will be described briefly.

Most of the prior art pupillary measuring devices are of a so-called closed-loop light measuring system in which the bundle of rays of visible light used to stimulate the pupillary light reflex has a diameter greater than the pupil diameter ("Outer Diameter Measuring Instrument, Electronic Pupil Meter, and Autonomic Nerve Function Examining Apparatus" <See, Japanese Laid-open Patent Publication No. 9-28672>, "Pathologic Diagnosing Apparatus" <See, Japanese Laid-open Patent Publication No. 10-28674>). According to the closed-loop system, since the bundle of light projected towards the pupil is greater than the pupil diameter, the total amount of light penetrating inwardly into the pupil subsequent to start of illumination of the visible light decreases as the pupil constricts. On the other hand, as the total amount of the light incident on the pupil decrease, the pupillary constriction is suppressed. As a result, the pupillary change tends to become blunt.

In contrast thereto, in order to examine a sharp pupillary change in reference to the reaction obtainable from the closed-loop system, a so-called open-loop measuring system has been suggested in which the bundle of visible light necessary to stimulate the pupillary light reflex is chosen to have a diameter smaller than the pupil diameter so that total amount of the visible light can illuminate inwardly of the pupil. (Reference: H. Hoshino, "Doukou Heikatsukin no Keitaigakuteki Tokushusei ni motoduku Tai-Hikari Hannou no Suurimoderu (Mathematical Model of Pupillary Light Reflex based on Morphological Particularity of Pupillary Smooth Muscle), Television Society Bulletin, Vol. 11, No. 8, pp. 1036–1042, 1994). It is, however, found that the open-loop system has a problem in that the illuminating beam tends to displace from the eye once the eye motion and the head motion take place and, as a result thereof, a portion or the total of the light deviates from the pupil. For this reason, with the prior art open-loop system, measurement is difficult to achieve and the subject is forcibly requested to fix the head and the eyes.

In the embodiment which will now be described, the pupillary measuring device 6 in which in the open-loop system, the illuminating light will not deviate from the pupil, the measurement is easy to achieve and no bearing is imposed on the subject will be described. Referring to a top plan view of the pupillary measuring device 6 shown in FIG. 22, the pupillary measuring device 6 includes a pair of bows 27, and a frame 29 connected with the bows 27. The pupillary measuring device 6 can be worn on the face of the subject, in a manner similar to the spectacles, with the bows 27 hung on the eyes. The pupillary measuring device 6 is so worn by the subject that the subject can view an interior of the frame 29. In FIG. 22, the subject's eyes E are shown for reference purpose. With the pupillary measuring device 6 worn on the subject's face, unless the frame 29 displaces relative to the subject's face, any possible displacement of such component parts as visible LEDs 10, Ir LEDs 20, translucent mirrors 22, CCD cameras 23, converging lenses 24 and so on which would otherwise result from the head motion can be avoided.

The frame of the pupillary measuring device 6 includes the visible LEDs 10, the Ir LEDs 20, the translucent mirrors 22, the CCD cameras 23 and the converging lenses 24. Those components are used one for each eye of the subject and are arranged having been separated by a separator 28 within the frame 28. The converging lenses 24 are used to collect the visible light emitted from the visible LEDs 10 and to reduce the respective diameters of the bundles of light to a value smaller than the pupil diameter. Functions of the other component parts than the converging lenses 24 are substantially identical to those of the component parts employed in the first embodiment of the present invention and are not therefore reiterated for the sake of brevity.

Arrangement of the component parts will now be described. The visible LEDs 10 are arranged in, for example, a matrix pattern at respective locations inwardly of one end of the frame 29 remote from the bows 27. The Ir LEDs 20 are fixed in position so that they can project infrared light towards the subject's eyes E. The number of the Ir LEDs 20 and the infrared outputs may be determined in consideration of the amount of natural light incident depending on the environment of use. The Ir LEDs 20 are so arranged that the subject's vision will not be hampered and the subject's attention will be directed to other targets to be watched. The translucent mirrors 22 are positioned at respective locations adjacent the subject's eyes E and remote from the associated converging lenses 24, in order to monitor the subject's eyes E with the CCD cameras 23 positioned out of the subject's field of vision and, also, in order to allow the visible light from the visible LEDs 10 to be projected towards the subject's eyes E. The CCD cameras 23 are fitted to left and right walls of the frame 29 so as to aim in a direction perpendicular to the optical axis of each of the converging lenses 24. It is to be noted that the CCD cameras 23 are connected with the calculating unit 3 (FIG. 11) and transmit image data to the calculating unit 3.

The calculating unit 3, based on the image data received from the CCD cameras 23, calculates the size of the pupil H of each of the subject's eyes E. Also, the calculating unit 3 can detect the amount of displacement of a center position of the pupil H within the image obtained from the CCD cameras 23. Detection of this amount of displacement will be described later. It is to be noted that as the size of the pupil H the pupil diameter (transverse or vertical diameter) or the surface area of the pupil may be calculated.

The lighting control unit 7, based on information on the amount of displacement of the center position of the pupil H, specify some of the visible LEDs 10 and turns them on. The specified visible LEDs 10 are those that the total amount of the visible light converged by the converging lenses 5 can be projected inwardly of the pupils H after the displacement has occurred in position. Thereby, even though the position of the pupil H displaces, the light bundle that has been converged can impinge inwardly of the pupil H at all times. Specific procedures for specifying some of the visible LEDs 10 to be turned on will be described later.

Hereinafter, the operation of the brain function examining apparatus 140 that is associated with the pupillary measuring device 6 and the lighting control 7 will be described. Referring to FIG. 22, with the pupillary measuring device 6, the IR LEDs 20 illuminate the subjects eyes E, and respective images of the subject's eyes E are imaged by the associated CCD cameras 23 through the corresponding translucent mirrors 22. The calculating unit 3 calculates the size of the pupil H based on the image data received from the CCD cameras 23 and also calculates the center position of the pupil H to calculate the amount of displacement in center position of the pupil H. If the translucent mirrors 22 are coated with anti-reflection film, the CCD cameras 23 will not be perceived by the subject.

Figure 23:
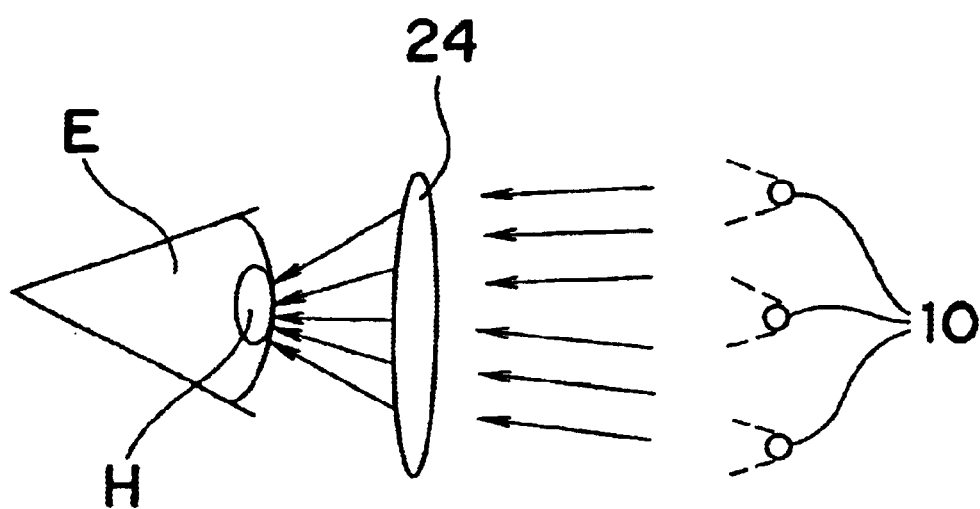
FIG. 23 is a schematic diagram showing the manner in which a bundle of light of a diameter smaller than the pupil diameter impinge upon the pupil H.
Figure 24:
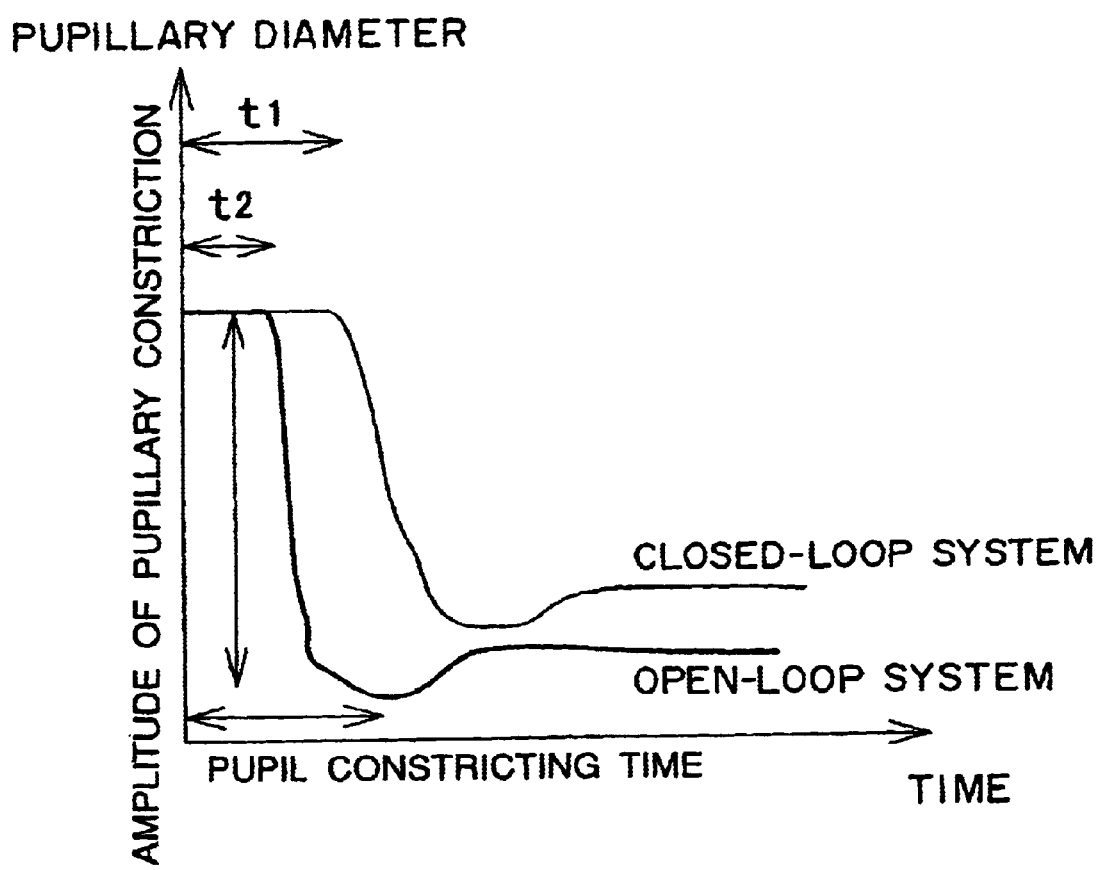
FIG. 24 is a graph showing change in size of the pupil H when the step light of any of an open-loop system and a closed-loop system is projected.

On the other hand, the lighting control 7, based on the amount of displacement in center position of the pupil H calculated by the calculating unit 3, turns on one of the visible LEDs 10 which is most suited to constitute an open-loop system. Rays of light emitted from the visible LED 10 then turned on are converged by the converging lens 24 to provide a bundle of light of a diameter smaller than the pupil diameter H which is in turn incident upon the subject's eye E. FIG. 23 illustrates the manner in which the bundle of light of a diameter smaller than the pupil diameter is incident on the pupil H. When the visible light from the visible LEDs 10 impinged upon the pupil H after having been converged by the converging lens 24, the pupil H generally undergoes constriction and the resultant pupillary light reflex can be observed. In other words, the open-loop system is defined in which since the diameter of the pupil H reduces, the amount of the incident light does not vary. On the other hand, in the case of the closed-loop system in which the bundle of light greater in diameter than the pupil diameter illuminates the pupil, the amount of the incident light decreases during constriction of the pupil, causing the pupil to redilate, variation of the the amplitude of constriction of the pupil H tends to be blunt. FIG. 24 illustrates a graph showing variation of the size of the pupil H when the step light (FIG.

2A) is projected by the open-loop system and the closed-loop system. From FIG. 24, it is possible to read out a characteristic of the pupil H. According to FIG. 24, as compared with the latency t1 of the closed-loop system, the latency t2 of the open-loop system employed in the illustrated embodiment of the present invention is short. In other words, the pupillary light reflex takes place immediately. Also, as compared with the closed-loop system, the open-loop system exhibits a relatively large amplitude of pupillary constriction and the pupil constricting time is also relatively short. Thus, as compared with the closed-loop system, the embodiment of the present invention constituting the open-loop system is effective to cause a sharp response.

Figure 25A:
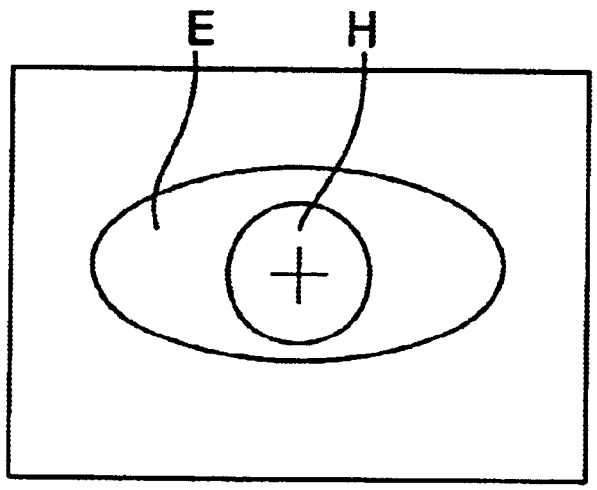
FIG. 25A is a diagram showing a screen when the center of the screen displaying the eye image of a CCD camera and a center position of the subject's pupil are aligned with each other.
Figure 25B:
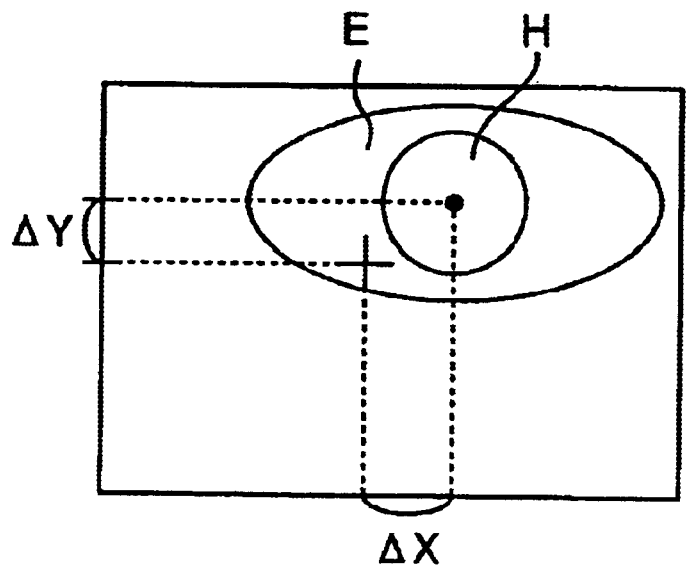
FIG. 25B is a diagram showing the case in which the subject's eye displace upwardly rightwardly relative to a frame.

Hereinafter, the method by which the calculating unit 3 (FIG. 22) detects the displacement of the center position of the pupil will be described. FIG. 25A illustrates a screen display in which the center of a screen displaying the image of the eye of the CCD camera 23 (FIG. 22) is aligned with the center position of the pupil H of the subject's eye E. In the event that the frame 29 (FIG. 22) displaces relative to the subject's head, or in the event that the eye viewing a certain fixed target undergoes motion, the image of the subjects eye E will displace up or down, left or right relative to the center of the screen. FIG. 25B illustrates the case in which the subject's eye E has displaced upwardly rightwardly relative to the center of the screen. This displacement can be quantitatively detected by an image processing or the like as an amount of displacement from the center. More specifically, the pupillary detector 31 (FIG. 1) of the calculating unit 3 detects the pupillary diameter. At this time, the coordinates for the center of the pupillary diameter can easily be determined. By calculating the difference between the coordinates for the center of the pupillary diameter and the coordinates for the center of the screen, the amount of displacement can be captured. In FIG. 25B, the amount of displacement is expressed by $\Delta X$ and $\Delta Y$ It is to be noted that in FIGS. 25A and 25B only one of the subject's eyes E has been shown. This is because in the event of the eye motion both eyes generally move the same amount in the same direction. Needless to say, the amount of displacement may be detected for each of the subject's eyes.

Figure 26A:
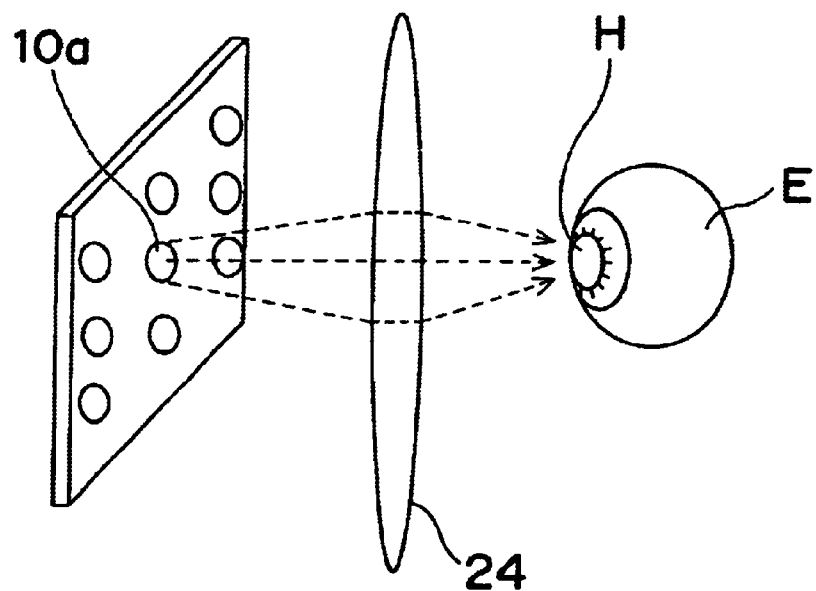
FIG. 26A is a diagram showing one of visible LEDs that is turned on when the subject's eye is not displaced relative to the center of the screen.
Figure 26B:
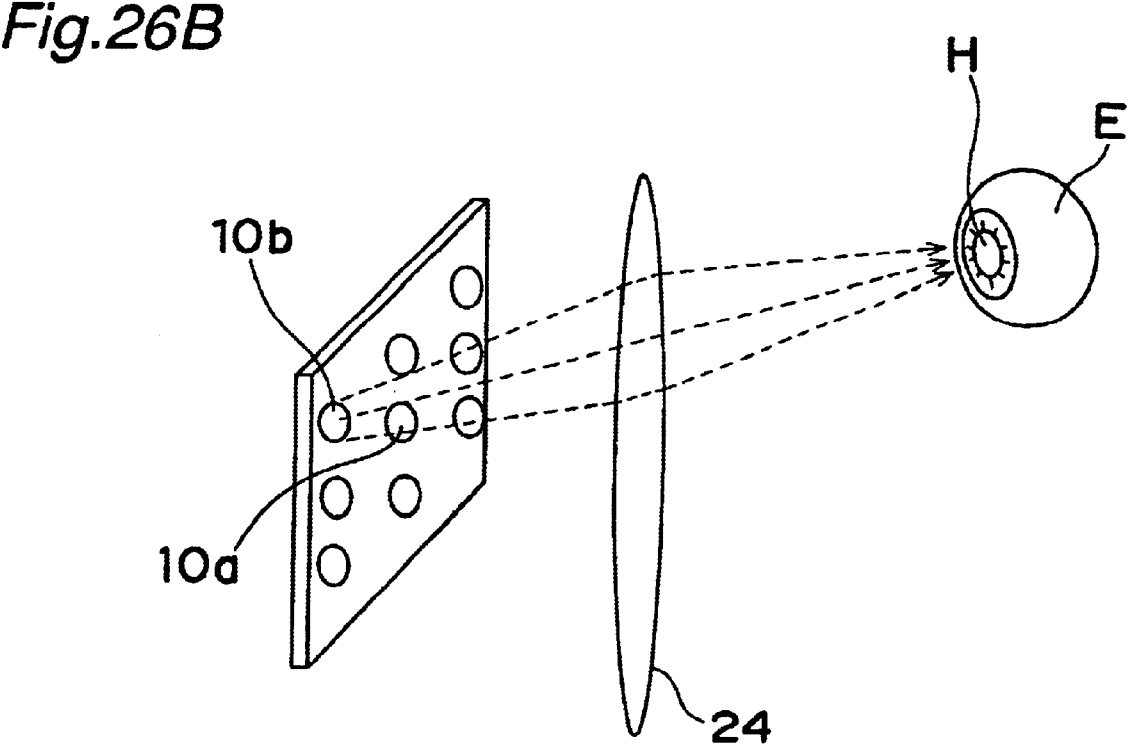
FIG. 26B is a diagram showing one of the visible LEDs that is turned on when the subject's eye is displaced upwardly rightwardly relative to the center of the screen.

In the next place, the procedures in which the lighting control 7 (FIG. 22) specifies some of the visible LEDs 10 (FIG. 22) to be turned on will now be described. FIG. 26A illustrates one 10a of the visible LEDs that is turned on in the event that the subject's eye E is not displaced relative to the center of the screen (FIG. 25A). Since no displacement occur between the respective centers of the subject's eye E and the screen, only one 10a of the visible LEDs 10 which is positioned at a center of the matrix arrangement of the LEDs 10 is turned on. FIG. 26B illustrates one 10b of the visible LEDs which is turned on in the event that the subject's eye E is displaced upwardly rightwardly relative to the center of the screen. Since the subject's eye E has displaced upwardly rightwardly, in place of the visible LED 10a the visible LED 10b positioned upwardly rightwardly thereof is turned on. The visible light emitted from the visible LED 10a or 10b is, after having been converged by the converging lens 24, projected onto the pupil H in the form of a light bundle of a diameter smaller than the pupillary diameter. Thus, by changing the visible LEDs 10 to be turned on, even though the subject's eye E moves or the frame 29 displaces with the center position of the pupil H out of alignment with the center of the screen, the total light flux converged by the converging lens 24 can impinge inwardly of the pupil H.

Figure 27A:
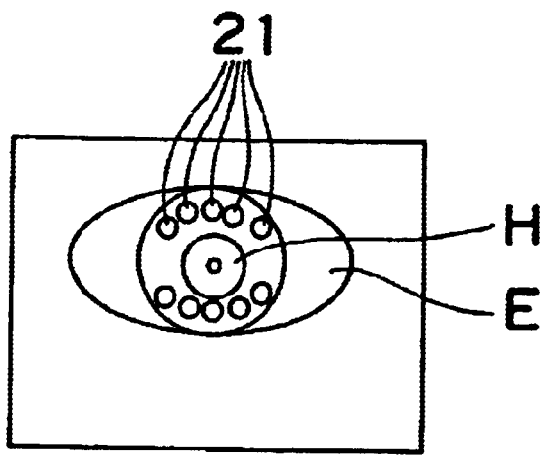
FIG. 27A is a diagram showing images of infrared LEDs reflected from the subject's eye when no displacement occurs.
Figure 27B:
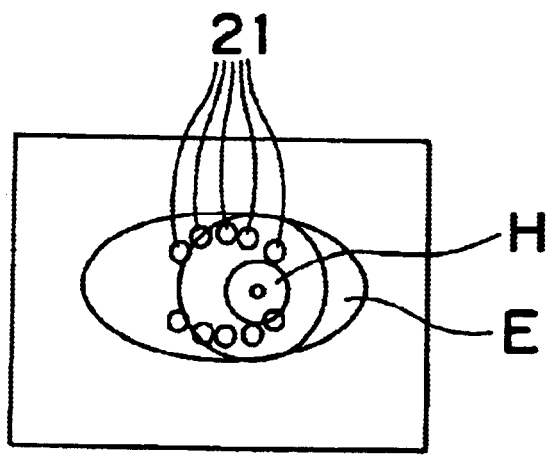
FIG. 27B is a diagram showing images of infrared LEDs reflected from the subject's eye when displacement occur.

The procedure in which the calculating unit 3 (FIG. 22) calculates the displacement of the pupil H from the center position using the visible light is such as hereinabove described. Another method can be contemplated to calculate the displacement. In other word, the amount of displacement of the center position of the pupil H may be calculated by detecting displacement of the center position of the pupil H relative to an image of the infrared LEDs 20 reflected from the cornea on an surface of the eye E. The method thereof will now be described. FIG. 27A illustrates the pupil H of the subject's eye E and an image 21 of the infrared LEDs 20 reflected from the eye E surface when no displacement occur. FIG. 27B illustrates the pupil H of the subject's eye E and an image 21 of the infrared LEDs 20 reflected from the eye E surface when displacement has occurred. Detection of a positional displacement of the pupil H by means of the infrared LEDs 20 requires calculation of a change in relative position between the center position of the pupil H and the virtual image (bright point) of the infrared LEDs 20. This can be accomplished by the image processing performed by the calculating unit 3 (FIG. 22). As shown in FIG. 27A, where the center of the pupil H of the eye E is aligned with the center of the screen of the CCD camera 7 (FIG. 22) (i.e., where no displacement occur), the virtual image (bright points) 21 of the infrared LEDs 20 reflected by the cornea appears above and below the pupil H. It is assumed here that the infrared LEDs 20 (FIG. 22) are arranged in upper and lower rows and that the CCD camera 23 is not provided with any infrared cut-off filter and can image an infrared region.

In the event that the frame 29 displaces, or the center position of the pupil H moves relative to the screen of the CCD camera 7 (FIG. 22) as a result of the eye motion, the relation in relative position between the center position of the pupil H and the virtual image (bright points) 21 of the infrared LEDs 20 on the cornea of the eye E varies from that shown in FIG. 27A. In FIG. 27B, there is shown the case in which the subject's eye E has moved in a rightward direction. By calculating the amount of variation as the amount of displacement, the amount of displacement in position can be detected as is the case with the visible light.

In the illustrated embodiment, FIG. 22 has been mainly described in connection with the pupillary measuring device 6 (FIG. 22) and the lighting control 7 (FIG. 22). The calculating unit 3, the database 4 and the display unit 5 of the brain function examining apparatus 140 (FIG. 22) may be identical with those described in connection with any one of the first to fourth embodiments. By way of example, the calculating unit 3 including the determining unit 33 (FIG. 10), the multivalue calculator 34 (FIG. 17), or the multivalue calculator 34 and the determining unit 35 (FIG. 21) can be employed.

In the foregoing description, the various embodiments of the present invention have been described.

According to the present invention, the index of the subject and the average index of a predetermined group are outputted (displayed), and it is possible to easily determine by the utilization of the relative relation displayed if the subject is suffering from, for example, a suspected dementia or the like. The indexes are values sufficiently representing the characteristic of the pupil defined variously in association with the pupillary change. Since examination of the subject's brain function is carried out by the use of those indexes, the brain function examination is possible with a handy method having no side-effect of the pupillary light reflex and it can be employed in the field of early diagnosis and clinical diagnosis of the brain disorder.

Also, according to the present invention, since the plural indexes are converted into as small discriminant scores as possible by means of the multivariate analysis, the targets to be handled can be reduced to facilitate a high speed processing. Since each makes use of the plural indexes sufficiently representing the characteristic of the pupil, the above described effects can also be obtained.

Furthermore, according to the present invention, the steady pupillary measurement can be carried out with respect to the pupillary light reflex of the open-loop system and there is no difficulty in measurement which would otherwise result from the head motion and the eye motion. As a result, without imposing any burden on the subject, the pupillary measurement making best use of the features of the open-loop system can be accomplished.

Although the present invention has been described in connection with the preferred embodiments thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A brain function examining apparatus for performing an examination of a brain function by detection of a pupillary size of a subject, which apparatus comprises:
    a) a light source for illuminating a pupil of the subject;
    b) a pupillary detector for detecting the pupillary size;
    c) an index calculating unit for calculating a subject index indicative of a characteristic of the pupil based on the pupillary size detected by the pupillary detector, wherein:
        c1) the characteristic of the pupil is a quality associated with variation of pupillary size; and
        c2) the subject index includes at least one of:
            pupillary constricting acceleration,
            maximum acceleration of pupillary constriction,
            time required to attain a maximum velocity of pupillary constriction,
            time required to attain a maximum velocity of pupillary redilation, and
            time required to attain a maximum acceleration of pupillary constriction;
    d) a database for storing a base index indicative of a characteristic of a pupil that can be used as a reference; and
    e) an output unit for outputting the subject index calculated by the index calculating unit, and the base index stored in the database, wherein:
        (1) the subject index calculated by the index calculating unit includes at least one of:
            latency,
            a natural size of the pupil,
            pupillary redilating time,
            amplitude of pupillary constriction,
            pupil constricting rate,
            pupil constricting velocity,
            maximum velocity of pupillary constriction,
            pupil redilating velocity, and
            maximum velocity of pupillary redilation;
        (2) the index calculating unit calculates a plurality of subject indexes;
        (3) the database stores a plurality of base indexes; and
        (4) the apparatus further comprises a multivalue calculator for calculating a first number of discriminant scores based on a second number of input values that is larger than the first number, the input values including the subject indexes calculated by the index calculating unit and the base indexes stored in the database.

2. The brain function examining apparatus as claimed in claim 1, wherein examination of the brain function is that of dementia.

3. The brain function examining apparatus as claimed in claim 1, wherein examination of the brain function is that of a degree of brain senescence.

4. The brain function examining apparatus as claimed in claim 1, further comprising:
    a determining unit for comparing the subject index calculated by the index calculating unit, with the base index stored in the database to determine a condition of the subject's brain function.

5. The brain function examining apparatus as claimed in claim 4, wherein the output unit also outputs a result of determination performed by the determining unit.

6. The brain function examining apparatus as claimed in claim 1, wherein:
    the multivalue calculator calculates base discriminant scores using the base indexes as the input values, and
    the apparatus further comprises a determining unit for comparing the subject discriminant scores calculated by the multivalue calculator, and the base discriminant scores to determine a condition of the subject's brain function.

7. The brain function examining apparatus as claimed in claim 6, wherein the output unit outputs at least one of the subject discriminant scores calculated by the multivalue calculator, the base discriminant scores and a result of determination performed by the determining unit.

8. The brain function examining apparatus as claimed in claim 1, wherein the database stores as the base index, the index indicative of the characteristic of the pupil of one of a normal case, an autonomic disorder case, a dementia case and an Alzheimer-type dementia case.

9. The brain function examining apparatus as claimed in claim 6, wherein the determining unit performs determination of one of a degree of senescence, autonomic activity, dementia and Alzheimer's disease of the subject.

10. The brain function examining apparatus as claimed in claim 1, wherein the light source emits a step light to the pupil.

11. The brain function examining apparatus as claimed in claim 1, wherein the light source emits a flash light to the pupil.

12. The brain function examining apparatus as claimed in claim 11, wherein the light source emits a flash light to the pupil for a duration shorter than a pupillary response latency.

13. The brain function examining apparatus as claimed in claim 1, wherein the light source emits a bundle of light of a size smaller than a minimum possible pupillary size.

14. The brain function examining apparatus as claimed in claim 1, wherein:
    the pupillary detector detects a time-based change of the pupillary size of the subject; and
    the index calculator is operable to determine a time-based change of an average pupillary size by calculating a mean of a plurality of time-based changes of the pupillary size detected by the pupillary detector and to calculate the subject index based on the average pupillary size.

15. The brain function examining apparatus as claimed in claim 1, wherein:
    the pupillary detector detects a time-based change of the pupillary size; and the index calculator is operable to determine a time-based change of an average pupillary size by moving-averaging a plurality of time-based changes of the pupillary size detected by the pupillary detector and to calculate the subject index based on the average pupillary size.

16. The brain function examining apparatus as claimed in claim 6, wherein the determining unit is operable to compare some of the subject indexes with some of the base indexes corresponding thereto and to determine, based on a result of comparison, one of progressive senescence of the subject's brain function and probability of the subject suffering from brain disorder.

17. The brain function examining apparatus as claimed in claim 1, wherein such some of the subject indexes and such some of the base indexes includes at least two of:
a natural size of the pupil,
latency,
pupillary redilating rate,
pupil constricting velocity,
maximum velocity of pupillary constriction,
pupil redilating velocity,
maximum velocity of pupillary redilation,
pupillary constricting acceleration, and
maximum acceleration of pupillary constriction.

18. The brain function examining apparatus as claimed in claim 17, wherein the determining unit determines one of progressive senescence of the subject's brain function and probability of the subject suffering from brain disorder in the event of at least one of situations:
in which the natural pupil size of the subject is small,
in which the latency is large,
in which the pupil constricting velocity is low,
in which the maximum velocity of pupillary constriction is low,
in which the pupil redilating velocity is low, and
in which the maximum velocity of pupillary redilation is low.

19. A brain function examining apparatus for performing an examination of a brain function by detection of a pupillary size of a subject, which apparatus comprises:
a) a light source for illuminating a pupil of the subject;
b) a pupillary detector for detecting the pupillary size;
c) an index calculating unit for calculating a plurality of subject indexes, each subject index indicative of a characteristics of the pupil based on the pupillary size detected by the pupillary detector;
d) a database for storing a plurality of base indexes, each base index indicative of a characteristic of a pupil that can be used as a reference;
e) a multivalue calculator for calculating a first number of discriminant scores based on a second number of input values that is larger than the first number, the input values including the subject indexes calculated by the index calculating unit and the base indexes stored in the database;
f) an output unit for outputting the subject index calculated by the index calculating unit, and the base index stored in the database.

20. The brain function examining apparatus as claimed in claim 19, wherein:
the multivalue calculator calculates base discriminant scores using the base indexes as the input values, and the apparatus further comprises a determining unit for comparing the subject discriminant scores calculated by the multivalue calculator, and the base discriminant scores to determine a condition of the subject's brain function.

21. The brain function examining apparatus as claimed in claim 20, wherein the output unit outputs at least one of the subject discriminant scores calculated by the multivalue calculator, the base discriminant scores and a result of determination performed by the determining unit.

22. The brain function examining apparatus as claimed in claim 20, wherein the determining unit performs determination of one of a degree of senescence, autonomic activity, dementia and Alzheimer's disease of the subject.

23. The brain function examining apparatus as claimed in claim 20, wherein the determining unit is operable to compare some of the subject indexes with some of the base indexes corresponding thereto and to determine, based on a result of comparison, one of progressive senescence of the subject's brain function and probability of the subject suffering from brain disorder.

24. The brain function examining apparatus as claimed in claim 23, wherein such some of the subject indexes and such some of the base indexes includes at least two of:
a natural size of the pupil,
latency,
pupillary redilating rate,
pupil constricting velocity,
maximum velocity of pupillary constriction,
pupil redilating velocity,
maximum velocity of pupillary redilation,
pupillary constricting acceleration, and
maximum acceleration of pupillary constriction.

25. The brain function examining apparatus as claimed in claim 24, wherein the determining unit determines one of progressive senescence of the subject's brain function and probability of the subject suffering from brain disorder in the event of at least one of situations:
in which the natural pupil size of the subject is small,
in which the latency is large,
in which the pupil constricting velocity is low,
in which the maximum velocity of pupillary constriction is low,
in which the pupil redilating velocity is low, and
in which the maximum velocity of pupillary redilation is low.

26. A brain function examining apparatus for performing an examination of a brain function for dementia by detection of a pupillary size of a subject, which apparatus comprises:
a) a light source for illuminating a pupil of the subject;
b) a pupillary detector for detecting the pupillary size;
c) an index calculating unit for calculating a subject index indicative of a characteristic of the pupil based on the pupillary size detected by the pupillary detector, wherein:
c1) the characteristic of the pupil is a quality associated with variation of pupillary size; and
c2) the subject index includes at least one of:
latency,
pupillary constricting acceleration,
maximum acceleration of pupillary constriction,
time required to attain a maximum velocity of pupillary constriction,
time required to attain a maximum velocity of pupillary redilation, and time required to attain a maximum acceleration of pupillary constriction;

d) a database for storing a base index indicative of a characteristic of a pupil that can be used as a reference; and e) an output unit for outputting the subject index calculated by the index calculating unit, and the base index stored in the database.

* * * * *

UNITED STATES PATENT AND TRADEMARK OFFICE
CERTIFICATE OF CORRECTION

PATENT NO. : 6,669,651 B1
DATED : December 30, 2003
INVENTOR(S) : Shogo Fukushima et al.

It is certified that error appears in the above-identified patent and that said Letters Patent is hereby corrected as shown below:

Column 7,
Line 23, change "II" to -- H --.

Column 10,
Line 34, change "noses" to -- noises --.

Column 23,
Line 36, change "$y_i=(y_{j1},...,y_{in})$" to -- $y_i=(y_{j1},...,y_{jn})$ --.
Line 52, change "$Dx=(z-x)A^-(z-x)^T$" to -- $Dx=(z-x)A^{-1}(z-x)^T$ --.
Line 53, change "A1" to -- $A^{-1}$ --.

Column 34,
Line 61, delete "latency,".

Signed and Sealed this

Thirteenth Day of July, 2004

JON W. DUDAS
*Acting Director of the United States Patent and Trademark Office*